(12) United States Patent
Kurth et al.

(10) Patent No.: US 9,585,692 B2
(45) Date of Patent: Mar. 7, 2017

(54) TRANSSEPTAL GUIDEWIRE

(71) Applicant: PRESSURE PRODUCTS MEDICAL SUPPLIES, INC., San Pedro, CA (US)

(72) Inventors: Paul Kurth, Santa Barbara, CA (US); Andrew W. Armour, Swarthmore, PA (US)

(73) Assignee: Pressure Products Medical Supplies Inc., San Pedro, CA (US)

( * ) Notice: Subject to any disclaimer, the term of this patent is extended or adjusted under 35 U.S.C. 154(b) by 0 days.

(21) Appl. No.: 13/934,985

(22) Filed: Jul. 3, 2013

(65) Prior Publication Data

US 2013/0296911 A1    Nov. 7, 2013

Related U.S. Application Data

(60) Division of application No. 12/152,377, filed on May 14, 2008, now Pat. No. 8,500,697, which is a
(Continued)

(51) Int. Cl.
*A61B 5/00* (2006.01)
*A61M 25/00* (2006.01)
(Continued)

(52) U.S. Cl.
CPC ......... *A61B 17/3468* (2013.01); *A61M 25/09* (2013.01); *A61M 25/09041* (2013.01);
(Continued)

(58) Field of Classification Search
CPC ............ A61M 25/09; A61M 25/09041; A61M 25/0905; A61M 25/065; A61M 2025/0293; A61M 2025/09166; A61M 2025/09175; A61M 2025/09133; A61M 2025/09141; A61M 2025/09041; A61B 2017/00243; A61B 2017/00247; A61B 2017/00331; A61B 2017/22044

See application file for complete search history.

(56) References Cited

U.S. PATENT DOCUMENTS

| | | | |
|---|---|---|---|
| 3,995,628 | A | 12/1976 | Gula et al. |
| 4,676,249 | A | 6/1987 | Arenas et al. |

(Continued)

FOREIGN PATENT DOCUMENTS

| | | |
|---|---|---|
| CA | 2212657 | 3/1998 |
| CA | 2244596 | 2/1999 |

(Continued)

OTHER PUBLICATIONS

Emile G. Daoud, MD, "Hands on Transseptal Catheterization", pp. 212-214, Heart Rhythm, vol. 2, No. 2, Feb. 2005.

(Continued)

*Primary Examiner* — Devin Henson
(74) *Attorney, Agent, or Firm* — RatnerPrestia

(57) ABSTRACT

A transseptal guidewire and methods for perforating the intra-atrial septum of the heart are disclosed. The transseptal guidewire has an elongated body, an end section biased in a curved configuration to define a proximal curve, and a distal section biased in a curved configuration to define a distal curve, the distal curve being oriented in a direction generally opposite that of the proximal curve.

35 Claims, 16 Drawing Sheets

Related U.S. Application Data continuation-in-part of application No. 11/875,365, filed on Oct. 19, 2007, now abandoned.

(51) Int. Cl.
*A61B 17/34* (2006.01)
*A61M 25/09* (2006.01)
*A61M 25/02* (2006.01)
*A61M 25/06* (2006.01)
*A61B 17/00* (2006.01)
*A61B 17/22* (2006.01)
*A61B 18/00* (2006.01)

(52) U.S. Cl.
CPC ........... *A61B 2017/00243* (2013.01); *A61B 2017/00247* (2013.01); *A61B 2017/00331* (2013.01); *A61B 2017/22044* (2013.01); *A61B 2018/00392* (2013.01); *A61M 25/065* (2013.01); *A61M 25/0905* (2013.01); *A61M 2025/0293* (2013.01); *A61M 2025/09133* (2013.01); *A61M 2025/09141* (2013.01); *A61M 2025/09166* (2013.01); *A61M 2025/09175* (2013.01); *A61M 2210/125* (2013.01)

(56) References Cited

U.S. PATENT DOCUMENTS

| | | |
|---|---|---|
| 4,724,846 A | 2/1988 | Evans, III |
| 5,007,434 A * | 4/1991 | Doyle ............... A61M 25/09 600/434 |
| 5,120,308 A | 6/1992 | Hess |
| 5,125,905 A | 6/1992 | Wright et al. |
| 5,190,528 A | 3/1993 | Fonger et al. |
| 5,273,042 A | 12/1993 | Lynch et al. |
| 5,279,573 A | 1/1994 | Klosterman |
| 5,282,479 A | 2/1994 | Havran |
| 5,312,341 A | 5/1994 | Turi |
| 5,366,444 A | 11/1994 | Martin |
| 5,370,609 A | 12/1994 | Drasler et al. |
| 5,403,338 A | 4/1995 | Milo |
| 5,438,993 A | 8/1995 | Lynch et al. |
| 5,454,785 A | 10/1995 | Smith |
| 5,484,419 A | 1/1996 | Fleck |
| 5,492,119 A * | 2/1996 | Abrams ............... A61N 1/0573 600/375 |
| 5,507,300 A | 4/1996 | Mukai et al. |
| 5,606,981 A * | 3/1997 | Tartacower ......... A61M 25/09 600/585 |
| 5,730,150 A | 3/1998 | Peppel et al. |
| 5,785,675 A | 7/1998 | Drasler et al. |
| 5,810,835 A | 9/1998 | Ryan et al. |
| 5,827,202 A | 10/1998 | Miraki et al. |
| 5,871,495 A | 2/1999 | Mueller |
| 5,895,404 A | 4/1999 | Ruiz |
| 5,968,059 A | 10/1999 | Ellis et al. |
| 5,976,164 A | 11/1999 | Bencini et al. |
| 5,989,278 A | 11/1999 | Mueller |
| 6,002,955 A | 12/1999 | Willems et al. |
| 6,011,988 A | 1/2000 | Lynch et al. |
| 6,045,565 A | 4/2000 | Ellis et al. |
| 6,059,484 A | 5/2000 | Greive |
| 6,063,082 A | 5/2000 | DeVore et al. |
| 6,093,185 A | 7/2000 | Ellis et al. |
| 6,096,001 A | 8/2000 | Drasler et al. |
| 6,123,084 A | 9/2000 | Jandak et al. |
| 6,129,697 A | 10/2000 | Drasler et al. |
| 6,216,573 B1 | 4/2001 | Moutafis et al. |
| 6,231,564 B1 | 5/2001 | Gambale |
| 6,238,406 B1 | 5/2001 | Ellis et al. |
| 6,258,061 B1 | 7/2001 | Drasler et al. |
| 6,290,709 B1 | 9/2001 | Ellis et al. |
| 6,402,740 B1 | 6/2002 | Ellis et al. |
| 6,416,490 B1 | 7/2002 | Ellis et al. |
| 6,423,027 B1 | 7/2002 | Gonon |
| 6,423,028 B1 | 7/2002 | Gonon |
| 6,451,017 B1 | 9/2002 | Moutafis et al. |
| 6,471,683 B2 | 10/2002 | Drasler et al. |
| 6,477,402 B1 | 11/2002 | Lynch et al. |
| 6,511,493 B1 | 1/2003 | Moutafis et al. |
| 6,537,266 B1 | 3/2003 | Mottola et al. |
| 6,544,209 B1 | 4/2003 | Drasler et al. |
| 6,551,281 B1 | 4/2003 | Raulerson et al. |
| 6,558,366 B1 | 5/2003 | Drasler et al. |
| 6,650,923 B1 | 11/2003 | Lesh et al. |
| 6,660,003 B1 | 12/2003 | DeVore et al. |
| 6,669,710 B2 | 12/2003 | Moutafis et al. |
| 6,676,627 B1 | 1/2004 | Bonnette et al. |
| 6,676,637 B1 | 1/2004 | Bonnette et al. |
| 6,689,089 B1 | 2/2004 | Tiedtke et al. |
| 6,692,456 B1 | 2/2004 | Eppstein et al. |
| 6,719,718 B2 | 4/2004 | Bonnette et al. |
| 6,749,617 B1 | 6/2004 | Palasis et al. |
| 6,755,803 B1 | 6/2004 | Bonnette et al. |
| 6,764,483 B1 | 7/2004 | Bonnette et al. |
| 6,805,684 B2 | 10/2004 | Bonnette et al. |
| 6,808,508 B1 | 10/2004 | Zafirelis et al. |
| 6,875,193 B1 | 4/2005 | Bonnette et al. |
| 6,890,353 B2 | 5/2005 | Cohn et al. |
| 6,899,712 B2 | 5/2005 | Moutafis et al. |
| 6,913,605 B2 | 7/2005 | Fletcher et al. |
| 6,926,726 B2 | 8/2005 | Drasler et al. |
| 6,945,951 B1 | 9/2005 | Bonnette et al. |
| 6,953,466 B2 | 10/2005 | Palasis et al. |
| 6,984,239 B1 | 1/2006 | Drasler et al. |
| 7,048,733 B2 | 5/2006 | Hartley et al. |
| 7,056,294 B2 | 6/2006 | Khairkhahan et al. |
| 7,083,588 B1 | 8/2006 | Shmulewitz et al. |
| 7,112,197 B2 | 9/2006 | Hartley et al. |
| 7,182,735 B2 * | 2/2007 | Shireman ............. A61M 25/09 600/585 |
| 7,455,646 B2 * | 11/2008 | Richardson ............. A61L 31/10 600/585 |
| 7,666,203 B2 | 2/2010 | Chanduszko |
| 8,182,432 B2 * | 5/2012 | Kim ..................... A61M 25/09 600/585 |
| 8,353,849 B2 * | 1/2013 | Tamai .................. A61M 25/09 600/585 |
| 2001/0001124 A1 | 5/2001 | Mueller |
| 2001/0051785 A1 | 12/2001 | Bonnette et al. |
| 2001/0051811 A1 | 12/2001 | Bonnette et al. |
| 2001/0056257 A1 | 12/2001 | Drasler et al. |
| 2002/0050197 A1 | 5/2002 | Moutafis et al. |
| 2002/0062091 A1 | 5/2002 | Jacobsen et al. |
| 2002/0143289 A1 | 10/2002 | Ellis et al. |
| 2002/0169377 A1 | 11/2002 | Khairkhahan et al. |
| 2002/0198550 A1 | 12/2002 | Nash et al. |
| 2003/0009166 A1 | 1/2003 | Moutafis et al. |
| 2003/0036712 A1 | 2/2003 | Heh et al. |
| 2003/0040763 A1 | 2/2003 | Moutafis et al. |
| 2003/0125660 A1 | 7/2003 | Moutafis et al. |
| 2003/0144657 A1 | 7/2003 | Bowe et al. |
| 2004/0015138 A1 | 1/2004 | Currier et al. |
| 2004/0039342 A1 | 2/2004 | Eppstein et al. |
| 2004/0049149 A1 | 3/2004 | Drasler et al. |
| 2004/0073141 A1 | 4/2004 | Hartley et al. |
| 2004/0092973 A1 | 5/2004 | Chanduszko |
| 2004/0122416 A1 | 6/2004 | Schweikert et al. |
| 2004/0143262 A1 | 7/2004 | Visram et al. |
| 2004/0153109 A1 | 8/2004 | Tiedtke et al. |
| 2004/0193046 A1 | 9/2004 | Nash et al. |
| 2004/0204672 A1 | 10/2004 | Palasis et al. |
| 2004/0206365 A1 | 10/2004 | Knowlton |
| 2004/0210194 A1 | 10/2004 | Bonnette et al. |
| 2004/0210214 A1 | 10/2004 | Knowlton |
| 2004/0210239 A1 | 10/2004 | Nash et al. |
| 2004/0230211 A1 | 11/2004 | Moutafis et al. |
| 2004/0267163 A1 | 12/2004 | Opie et al. |
| 2005/0033334 A1 | 2/2005 | Santra et al. |
| 2005/0065507 A1 | 3/2005 | Hartley et al. |
| 2005/0101984 A1 * | 5/2005 | Chanduszko ......... A61B 17/0057 606/185 |

(56) References Cited

U.S. PATENT DOCUMENTS

| | | |
|---|---|---|
| 2005/0149097 A1 | 7/2005 | Regnell et al. |
| 2005/0159738 A1 | 7/2005 | Visram et al. |
| 2005/0222557 A1 | 10/2005 | Baxter et al. |
| 2005/0222558 A1 | 10/2005 | Baxter et al. |
| 2005/0228468 A1 | 10/2005 | Macoviak et al. |
| 2005/0234436 A1 | 10/2005 | Baxter et al. |
| 2005/0245847 A1 | 11/2005 | Schaeffer |
| 2005/0251105 A1 | 11/2005 | Peyman et al. |
| 2005/0256450 A1 | 11/2005 | Palasis et al. |
| 2005/0283150 A1 | 12/2005 | Moutafis et al. |
| 2006/0009715 A1 | 1/2006 | Khairkhahan et al. |
| 2006/0009737 A1 | 1/2006 | Whiting et al. |
| 2006/0047267 A1 | 3/2006 | Gately et al. |
| 2006/0064062 A1* | 3/2006 | Gurusamy .......... A61M 25/065 604/170.03 |
| 2006/0064123 A1 | 3/2006 | Bonnette et al. |
| 2006/0074398 A1 | 4/2006 | Whiting et al. |
| 2006/0079769 A1 | 4/2006 | Whiting et al. |
| 2006/0079787 A1 | 4/2006 | Whiting et al. |
| 2006/0079870 A1 | 4/2006 | Barry |
| 2006/0095015 A1 | 5/2006 | Hobbs et al. |
| 2006/0095052 A1 | 5/2006 | Chambers |
| 2006/0116609 A1* | 6/2006 | Kanuka ................. A61M 25/09 600/585 |
| 2006/0122680 A1 | 6/2006 | Auth et al. |
| 2006/0200113 A1 | 9/2006 | Haffner et al. |
| 2006/0241648 A1 | 10/2006 | Bleich et al. |
| 2007/0032746 A1* | 2/2007 | Sell .................. A61M 25/0127 600/585 |
| 2007/0043307 A1 | 2/2007 | Raulerson et al. |
| 2007/0185413 A1 | 8/2007 | Asai et al. |
| 2007/0270741 A1 | 11/2007 | Hassett et al. |
| 2009/0105724 A1* | 4/2009 | Yoshizaki .......... A61M 25/0041 606/129 |
| 2010/0106177 A1 | 4/2010 | Chanduszko |
| 2010/0114140 A1 | 5/2010 | Chanduszko |

FOREIGN PATENT DOCUMENTS

| | | |
|---|---|---|
| CA | 2322452 | 9/1999 |
| CA | 2499753 | 4/2004 |
| DE | 9212575.1 | 11/1992 |
| EP | 0470781 | 2/1992 |
| EP | 0554754 A | 8/1993 |
| EP | 0 587 984 A1 | 3/1994 |
| EP | 829239 | 3/1998 |
| EP | 0 842 673 A1 | 5/1998 |
| EP | 0873719 | 10/1998 |
| EP | 895752 | 2/1999 |
| EP | 1484025 | 12/2004 |
| EP | 1542593 A2 | 6/2005 |
| EP | 1570878 | 9/2005 |
| EP | 1602339 | 12/2005 |
| EP | 1 920795 A1 | 5/2008 |
| GB | 2263407 | 7/1993 |
| JP | 10225459 | 8/1998 |
| MX | PA02010065 | 3/2003 |
| WO | WO9324830 | 12/1993 |
| WO | WO9410917 | 5/1994 |
| WO | WO 97/47350 A | 12/1997 |
| WO | WO9839038 | 9/1998 |
| WO | WO9922655 | 5/1999 |
| WO | WO9933510 | 7/1999 |
| WO | WO9944523 | 9/1999 |
| WO | WO9944524 | 9/1999 |
| WO | WO0150966 | 7/2001 |
| WO | WO0178596 | 10/2001 |
| WO | WO 03/008005 | 1/2003 |
| WO | WO03045259 | 6/2003 |
| WO | WO03063942 | 8/2003 |
| WO | WO03077733 | 9/2003 |
| WO | WO2004026147 | 4/2004 |
| WO | WO2006/060019 | 6/2006 |
| WO | WO2006094222 | 9/2006 |
| WO | WO 2006/119503 A1 | 11/2006 |
| WO | WO2005/046487 | 5/2007 |

OTHER PUBLICATIONS

John Hummel, MD, FACC, Transseptal Catheterization With Intracardiac Echocardiography (ICE), pp. 1-6, Technology Focus, Published Oct. 12, 2004.

Takayuki Hirano, MD Makoto Komatsu, MEng , Toshiro Saeki, BSc, Hiroshi Uenohara, MD, Akira Takahashi, MD[4] , Kazuyoshi Takayama, DEng, Takashi Yoshimoto, MD, "Enhancement of Fibinolytics With a Laser-Induced Liquid Jet", Medline, Jun. 11, 2001, Wiley-Liss.

Douek PC, Gandjbakche A, Leon MB, Bonner RF, "Functional Properties of a Prototype Rheolytic Catheter for Percutaneous Thrombectomy. In Vitro Investigations.", pp. 547-552, InvestRadiol, May 29, 1994.

International Search Report dated Jan. 22, 2009, application No. PCT/US2008/080123.

International Search Report dated Apr. 3, 2009, application No. PCT/US2009/030703.

European Communication, dated Aug. 22, 2012, corresponding to European Patent Application No. 08 839 113.1-1526, based on PCT/US2008/080123.

European Office Action in European Patent Application No. 08 839 113.1-1506, Mail Date: Dec. 21, 2015

\* cited by examiner

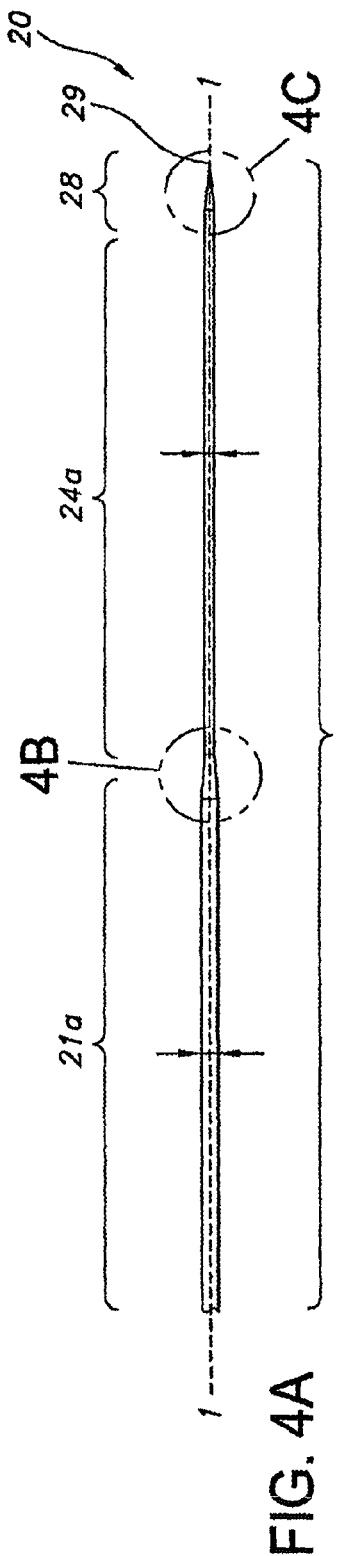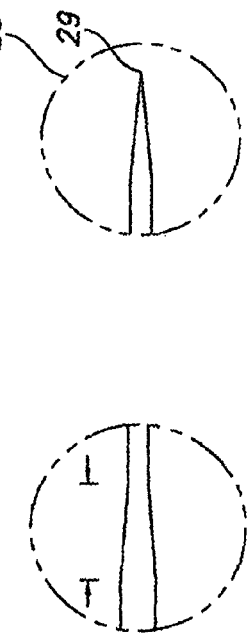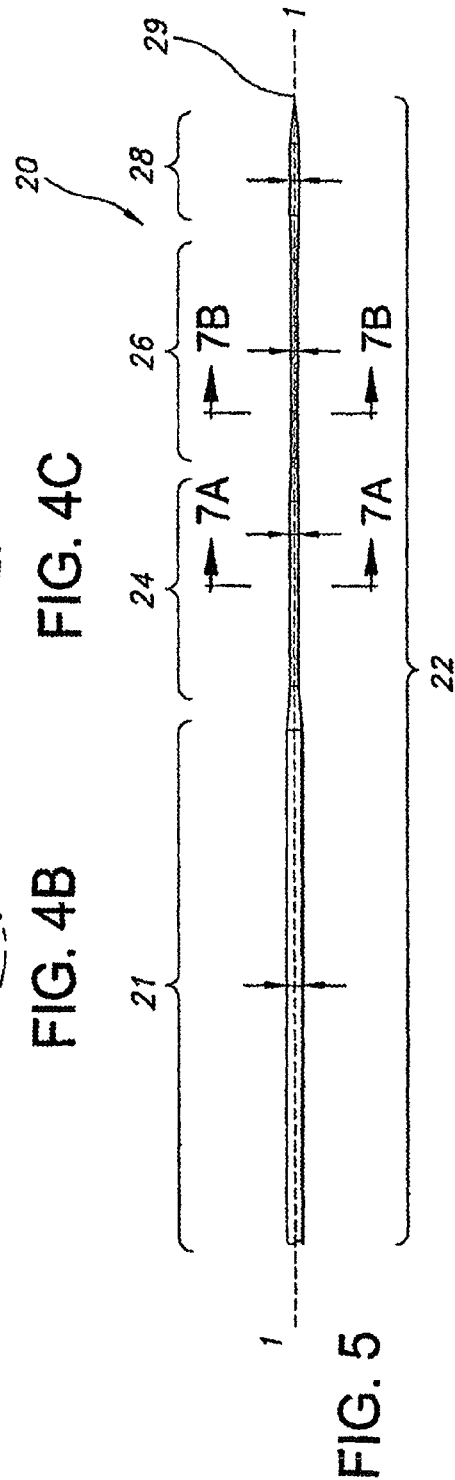

TRANSSEPTAL GUIDEWIRE

CROSS REFERENCE TO RELATED APPLICATIONS

This is a Divisional application which claims priority to U.S. application Ser. No. 12/152,377, filed May 14, 2008, which is a continuation-in-part application claiming priority to U.S. non-provisional application Ser. No. 11/875,365, filed Oct. 19, 2007, the entire disclosures of each of these applications being incorporated herein by reference for all purposes. International patent application PCT/US2008/080123, filed Oct. 16, 2008 and claiming priority to U.S. application Ser. No. 12/152,377, is also incorporated herein by reference in its entirety for all purposes.

FIELD OF THE INVENTION

The present invention relates generally to less invasive surgical equipment and surgical procedures. More particularly, the present invention relates to devices and methods for crossing from the right atrium to the left atrium by perforating the intra-atrial septum of the heart for the treatment of intracardiac arrhythmias and defects such as, for example, atrial fibrillation and valve defects related to cardiac disease as well as for pacing, ablating, and correction of other structural defects.

BACKGROUND OF THE INVENTION

Since the 1950's, transseptal procedures of the heart have been traditionally performed using Brockenbrough needles in which a puncture is made through an intact atrial septum from the right atrium to the left atrium. Several risks, however, have been associated with the use of Brockenbrough needles. One risk is the perforation of the lateral atrial wall after crossing the atrial septum. Another risk is the potential perforation of the aortic root.

Attempts have been made to reduce these and other risks. For example, U.S. Pat. No. 5,312,341 relates to the problem of inadvertent withdrawal of a catheter tip from the left atrium, through the atrial septum, and back into the right atrium. A retaining means for retaining the distal tip of a sheath which has been placed through a septum, such as the interatrial septum, across the septum, in the left atrium during left heart procedures was therefore proposed.

U.S. Pat. No. 6,650,923 relates to a method for accessing the left atrium by locating the fossa ovalis of the intra-atrial septum. An access catheter with a detector for identifying and providing access through the fossa ovalis was proposed.

U.S. Patent Publication No. 2006/0064062 relates to transseptal puncture needles and transseptal puncture needle assemblies. More specifically, it relates to curved transseptal puncture needles and needle assemblies that facilitate insertion through curved transseptal introducers. Each curved transseptal puncture needle includes a needle tip with a tangential back bevel configuration, a reverse tangential back bevel configuration, or a conical reverse bevel configuration.

U.S. Patent Publication No. 2005/0101984 relates to septal puncture in patients in which a communication is present between the two atria of the heart, for example, a patient with a patent foramen ovale (PFO). A device and method are proposed to safely puncture both an intact atrial septum and an atrial septum having a PFO. The proposed device includes a blunt outer needle, and a second inner needle disposed longitudinally through the lumen of the outer needle, wherein the inner needle is flexible, e.g., has a flexible portion and/or a bend or other non-traumatic conformation at its tip.

U.S. Patent Publication Nos. 2005/0159738 and 2005/0065507 relate to devices for septal perforation utilizing radio frequency energy. Each device includes a functional tip with at least one active electrode capable of creating a controlled perforation in body tissue. The device is introduced into the right atrium and the functional tip is positioned against the atrial septum. Energy is applied to the tip to create the perforation.

U.S. Pat. No. 6,890,353 relates to a method and apparatus for reducing mitral regurgitation by applying a force to the wall of the coronary sinus so as to force the posterior leaflet anteriorly and thereby reduce mitral regurgitation. A guidewire uses a sharp tip for allowing the distal end of a guidewire to penetrate tissue.

U.S. Patent Publication No. 2006/0241648 relates to methods and apparatus for modifying tissue. The proposed method includes advancing a beveled distal tip of a guide member to facilitate advancement of the guide member through tissue. A modification device is advanced along the guide member.

Nevertheless, there remains a need for improved devices and methods for perforating the intra-atrial septum of the heart with devices that improve the safety of the procedure.

SUMMARY OF THE INVENTION

In one aspect, a transseptal guidewire configured to perforate the intra-atrial septum is provided. The transseptal guidewire has an elongated body, an end section biased in a curved configuration to define a proximal curve, and a distal section biased in a curved configuration to define a distal curve, the distal curve being oriented in a direction generally opposite that of the proximal curve.

In another aspect, a system configured to perforate the intra-atrial septum is provided. The transseptal access system includes a wall defining a lumen extending from a proximal section to a distal opening. The lumen is reduced in size from a first diameter in the proximal section to a second diameter at the distal opening that is smaller than the first diameter. A transseptal guidewire is configured to be inserted into the lumen of the transseptal access system. The transseptal guidewire has a distal section with a longitudinal axis and a perforating tip laterally offset from the longitudinal axis. The perforating tip of the transseptal guidewire is configured to be offset from the wall of the transseptal access system a distance that is equal to or smaller than the second diameter of the lumen of the transseptal access system, thereby reducing or avoiding contact between the perforating tip of the transseptal guidewire and the wall as the perforating tip is advanced distally through the distal opening of the transseptal access system.

In yet another aspect, a system configured to perforate the intra-atrial septum is provided having a transseptal access system including a wall defining a lumen that has a first section with a first diameter and a second section with a second diameter smaller than the first diameter. A transition step is defined between the first and second sections. A transseptal guidewire is configured to be inserted within the lumen of the transseptal access system, the transseptal guidewire having an elongated body and a distal section. The distal section has a longitudinal axis and a perforating tip laterally offset from the longitudinal axis. The perforating tip of the transseptal guidewire is configured to be offset from the wall of the transseptal access system a distance that is equal to or larger than the transition step defined between the first and second sections of the lumen, but equal to or smaller than the sum of the transition step and the second diameter. Thus, contact between the perforating tip and the transition step is reduced as the perforating tip is advanced through the lumen from the first section to the second section of the lumen.

In still another aspect, a system configured to perforate the intra-atrial septum is provided having a transseptal access system defining a lumen, the lumen having a first section with a first diameter, a second section with a second diameter smaller than the first diameter, and a transition step defined between the first section and second section. A transseptal guidewire is configured to be inserted within the lumen of the transseptal access system. The transseptal guidewire has an elongated body, an end section biased in a curved configuration to define a proximal curve, a distal section biased in a curved configuration to define a distal curve, and a distal perforating tip. The distal curve is oriented in a direction generally opposite that of the proximal curve, thereby avoiding contact between the perforating tip and the transition step as the perforating tip is advanced through the lumen from the first section to the second section of the lumen.

In another aspect, a system configured to perforate the intra-atrial septum is provided having a transseptal access system defining a lumen having a first section with a first diameter, a second section with a second diameter smaller than the first diameter, and a transition step defined between the first section and second section. A transseptal guidewire is configured to be inserted within the lumen of the transseptal access system and has an elongated body, a perforating tip, and means for avoiding or reducing contact between the perforating tip and the transition step as the perforating tip is advanced through the lumen from the first section to the second section of the lumen.

In yet another aspect, a method of perforating the intra-atrial septum is provided. The method includes introducing a transseptal access system toward the intra-atrial septum. A transseptal guidewire is constrained within a lumen of the transseptal access system such that a proximal curve defined in an end section of the transseptal guidewire and a distal curve defined in a distal section of the transseptal guidewire are oriented in generally opposite directions. The transseptal guidewire is then advanced from a first section of the lumen having a first diameter to a second section of the lumen having a second diameter smaller than the first diameter, while avoiding contact between a perforating tip of the transseptal guidewire and a transition step defined between the first section and second section of the lumen.

In still another aspect, a method of forming a transseptal guidewire configured to perforate the intra-atrial septum is provided. The method includes forming a proximal curve in an end section of an elongated body that it is biased in a curved configuration. A distal curve is formed in a distal section of the elongated body so the distal curve is biased in a curved configuration and oriented in a direction generally opposite that of the proximal curve.

BRIEF DESCRIPTION OF THE DRAWING

The invention is best understood from the following detailed description when read in connection with the accompanying drawings, with like elements having the same reference numerals. This emphasizes that according to common practice, the various features of the drawings are not drawn to scale. On the contrary, the dimensions of the various features are arbitrarily expanded or reduced for clarity. Included in the drawings are the following figures:

FIG. 4A is a side view of the transseptal guidewire of FIG. 3 in an intermediate stage of fabrication according to an exemplary method of fabricating the transseptal guidewire;

FIG. 4B is an enlarged view of a tapered portion of the transseptal guidewire shown in FIG. 4A;

FIG. 4C is an enlarged view of a tapered distal section of the transseptal guidewire shown in FIG. 4A;

FIG. 5 is a side view of the transseptal guidewire illustrated in FIG. 4A in is another intermediate stage of fabrication according to an exemplary method of fabricating the transseptal guidewire;

DETAILED DESCRIPTION OF THE INVENTION

Figure 1:
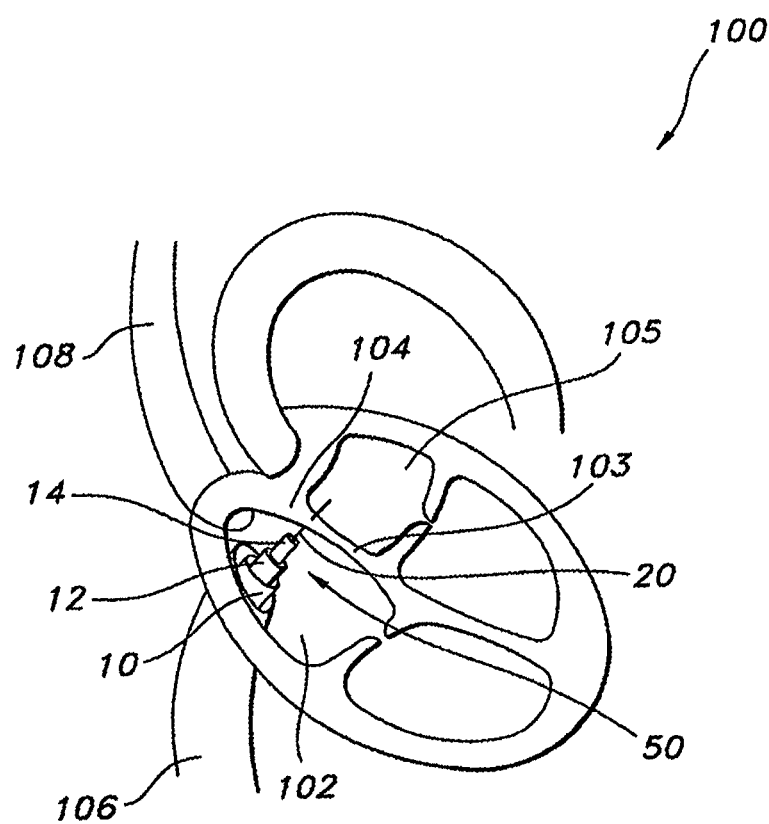
FIG. 1 is a schematic representation of a heart showing an embodiment of a transseptal trocar device positioned within the heart.

Aspects of the invention will now be described with reference to the figures. Such figures are intended to be illustrative rather than limiting and are included herewith to facilitate the explanation of the present invention.

Referring generally to the figures (FIGS. 1-9), in accordance with an exemplary embodiment, a transseptal guidewire 20 configured to perforate the intra-atrial septum 104 of the heart 100 is provided. The transseptal guidewire 20 has an elongated body 22, an end section 26, and a tapered distal section 28. At least a portion of the end section 26 has a first dimension X in a first direction transverse to a longitudinal axis 1 of the elongated body 22 that is larger than a second dimension Y in a second direction transverse to the longitudinal axis 1. In an exemplary embodiment, when the transseptal guidewire 20 perforates the intra-atrial septum 104 and extends into the left atrium 105, the end section 26 is biased in a curved configuration to help render end section 26 atraumatic so as to prevent perforation of the left atrial wall.

Referring now to the individual figures in detail, FIG. 1 depicts a schematic representation of a heart 100 having a transseptal trocar device 50 positioned within heart 100. The transseptal trocar device 50 is configured to perform transseptal catheterizations for access into the left atrium 105 of heart 100 from the right atrium 102 by way of either the inferior vena cava 106 or superior vena cava 108 which supply blood into the right atrium 102 of heart 100.

By a method described in greater detail below, the transseptal trocar device 50, which includes a transseptal sheath 10, dilator 12, outer needle 14, and transseptal guidewire 20, is placed against a septum, such as the intra-atrial septum 104. In an exemplary embodiment, when the distal tip of outer needle 14 is properly positioned in contact with the thin walled fossa ovalis 103 of the intra-atrial septum 104, transseptal guidewire 20 is abruptly extended from the lumen of outer needle 14 to perforate the fossa ovalis 103. Following penetration of the intra-atrial septum 104, and without changing the position of outer needle 14, the distal tip of dilator 12, along with the distal tip of transseptal sheath 10 is passed through the septum and into the left atrium 105.

At times, dilator 12 and sheath 10 do not have sufficient stiffness to pass through the perforation hole (not shown) made in the fossa ovalis 103. In such instances, outer needle 14 may be passed over the guidewire 20 to dilate the septum prior to inserting dilator 12 and sheath 10 through the perforation. The outer needle 14 can also provide support while dilator 12 and sheath 10 are advanced beyond outer needle 14 and through the perforation hole into the left atrium 105. In another embodiment, dilator 12 is optionally made from material that provides sufficient support during the transseptal perforation procedure and the outer needle 14 may not be needed and can be eliminated from device 50.

Figure 2:
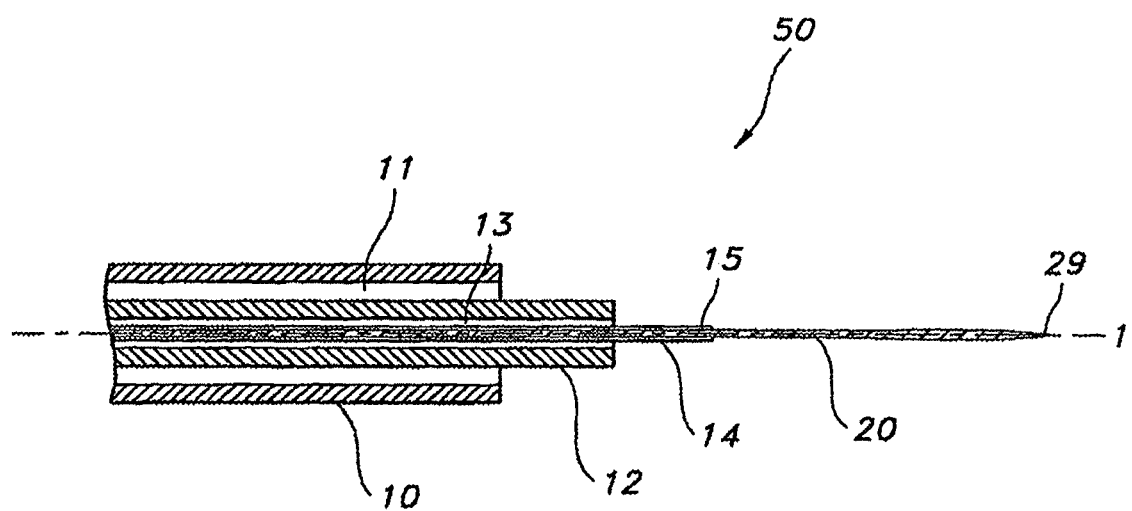
FIG. 2 is a cross-sectional side view of the transseptal trocar device shown in FIG. 1.

Referring now to FIGS. 1 and 2, aspects of the transseptal trocar device 50 will be described in further detail. Transseptal trocar device 50 includes a transcutaneous intravascular sheath 10 through which components of the device 50 pass from outside the patient's body through a vessel, for example, the femoral vein, through the inferior vena cava 106 into the right atrium 102. Alternatively, sheath 10 may be advanced through a vessel located at an upper half of the body, such as the subclavian vein, through the superior vena cava 108 into the right atrium 102. The sheath 10 and/or other components of transseptal trocar device 50 may have a fixed curve or may be steerable by actuators on a control handle (not shown) located at a proximal end of sheath 10 to aid in delivering the device 50 along the vascular path leading to the patient's right atrium 102.

According to an exemplary embodiment, sheath 10 is made from soft polymer materials such that sheath 10 is pliable and atraumatic when advanced through vasculature. For example, polymers such as polyimide, polyamide, polyetherblockamide, polyethylene, polytetrafluoroethylene (PTFE), fluorinated ethylene propylene (FEP), and polyurethane may be used. Other biocompatible polymer materials that minimize damage to tissue during the delivery of device 50 to the right atrium 102 may also be used. Transseptal trocar device 50 also includes a dilator 12 slidingly positioned within a sheath lumen 11 of sheath 10 axially disposed along longitudinal axis 1. Dilator 12 is configured to dilate a perforation hole (not shown) made in the intra-atrial septum 104 to provide improved access for the sheath 10 into the left atrium 105. In an exemplary embodiment, the distal end of dilator 12 may be blunted or tapered (not shown) toward outer needle 14 to provide gradual dilation of the perforation hole as dilator 12 is slidingly advanced into the left atrium 105.

As shown in FIG. 2, dilator 12 includes a lumen 13 which receives outer needle 14. Outer needle 14 has a distal end that contacts intra-atrial septum 104 to position outer needle 14 against fossa ovalis 103. In an exemplary embodiment, outer needle 14 is similar in size to a Brockenbrough needle, e.g., with tip diameter of about 0.8 mm. Outer needle 104 also includes a lumen 15 to receive and provide structural columnar support for a septal perforator, such as a transseptal guidewire 20 axially disposed within lumen 15. The inner diameter of lumen 15 typically approximates the maximum outer diameter of transseptal guidewire 20 such that the transseptal guidewire 20 is slidable within outer needle 14. In certain embodiments, the outer diameter of outer needle 14 gradually tapers toward transseptal guidewire 20 to also function as a dilator of the perforation hole (not shown) created in the fossa ovalis 103.

According to an exemplary embodiment, dilator 12 and outer needle 14 may be made of a polymer material, as described above. Other materials that provide sufficient support during the transseptal procedure are contemplated. For example, various metals, such as nitinol, steel, or titanium, or alloys thereof may be used.

Figure 3:
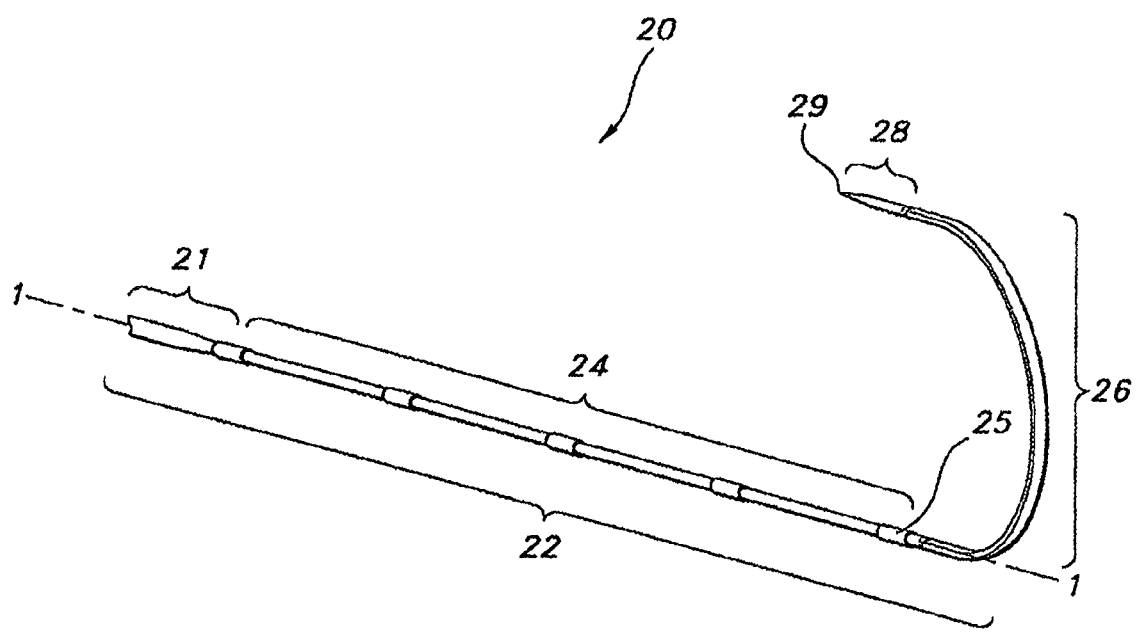
FIG. 3 is a perspective view of a transseptal guidewire of the transseptal trocar device according to one exemplary embodiment of the invention.

Referring now to FIGS. 2 and 3, aspects of the transseptal guidewire 20 according to one exemplary embodiment of the present invention are described in further detail. Transseptal guidewire 20 is configured to perforate the intra-atrial septum 104 and is disposed within lumen 15 so that transseptal guidewire 20 is reciprocally and axially moveable within outer needle 14. If necessary, the transseptal guidewire 20 can be rotated as well. Transseptal guidewire 20 has a length longer than outer needle 14, for example about 15 cm longer than outer needle 14 such that transseptal guidewire 20 has an overall length that is longer than about 117.5 cm, though other dimensions are contemplated as well. In another embodiment, transseptal guidewire 20 has a length that is about 50 cm longer than outer needle 14. The diameter of transseptal guidewire 20 is sized to fit through the lumen 15 of commercially available transseptal outer needles 14. For instance, the diameter of transseptal guidewire 20 is less than the diameter of lumen 15 of outer needle 14 so transseptal guidewire 20 may pass through outer needle 14 with little or no resistance.

Now referring to FIG. 3, the transseptal guidewire 20 includes an elongated body 22, an end section 26, and a tapered distal section 28. The tapered distal section 28 terminates at a pointed tip 29 at the distal end of transseptal guidewire 20. In an exemplary embodiment, when transseptal guidewire 20 is positioned fully within outer needle 14, transseptal guidewire 20 retains a substantially straight configuration. When transseptal guidewire 20 extends through the distal end of lumen 15 along longitudinal axis 1, end section 26 is no longer supported within outer needle 14 and flexes to a curved conformation such as that shown for illustration purposes in FIG. 3. Thus, in use, when the distal end of outer needle 14 contacts intra-atrial septum 104, transseptal guidewire 20 may extend so that pointed tip 29 perforates intra-atrial septum 104 and is positioned in left atrium 105. As transseptal guidewire 20 continues its path along axis 1 into left atrium 105, end section 26 curves into a non-traumatic conformation so that the lateral wall of the left atrium 105 is not exposed to pointed tip 29. Preferably, the tip 29 is sufficiently flexible so that it does not need the curve to be atraumatic.

In an exemplary embodiment, transseptal guidewire 20 may be coated with a material to ease insertion through the lumen 15 of commercially available transseptal outer needles 14 and/or to prevent clots from forming on the guidewire 20. For example, the entire length of transseptal guidewire 20 or a portion of its length may be coated with a material that has antithrombogenic properties to prevent clots from forming on the wire. Exemplary coatings may be hydrophobic or hydrophilic. Typical coatings may be formed from Teflon, a silicone fluid, or urethane based polymers. Other biocompatible coatings that provide the above mentioned properties may also be used.

As will be described in further detail below, a portion of end section 26 is ovalized such that end section 26 has a substantially non-circular cross section. Ovalizing a portion of end section 26 partly assists with biasing end section 26 in a curved configuration such as that shown in FIG. 3.

As also illustrated in FIG. 3, elongated body 22 of transseptal guidewire 20 has a portion 24 proximal of end section 26. Portion 24 has a substantially circular cross section relative to end section 26. In one embodiment, portion 24 is an imagable section having radiopaque markers 25a-e coupled to the imagable section 24. Radiopaque markers 25a-e may be made of a platinum/iridium alloy and are sufficiently visible under fluoroscopy (x-ray) to assist with imaging of the operative area. In one embodiment, the radiopaque markers 25a-e are formed by a platinum coating or cladding. Other radiopaque materials may also be used such as palladium, gold, silver, tungsten, etc.

In an exemplary embodiment, when a portion of imagable section 24 extends into the left atrium 105 from the perforation hole (not shown), x-ray imaging of radiopaque markers 25a-e may confirm successful perforation of the intra-atrial septum 104. Radiopacity of markers 25a-e is generally equal to, or greater than, transseptal needle 20, thus eliminating the need for radiopaque contrast solution.

Radiopaque markers 25a-e are retained on imagable section 24 since end section 26 is ovalized and has a dimension (such as a width) greater than the diameter of imagable section 24. Additionally, a portion 21 of elongated body 22 proximal to imagable section 24 has a tapered transition to imagable section 24 with a diameter also greater than the diameter of imagable section 24. Thus, radiopaque markers 25a-e are retained to imagable section 24 between adjacent portion 21 and end section 26.

Referring now to FIGS. 4A-C, 5, and 6, a method of fabricating a transseptal guidewire 20 of the present invention is illustrated. As shown in FIG. 4A, which illustrates an intermediate configuration of transseptal guidewire 20 during the manufacturing process, transseptal guidewire 20 has an elongate body 22a disposed along longitudinal axis 1 of transseptal guidewire 20. Transseptal guidewire 20 is optionally made from various metals such as, for example, nitinol, steel, or titanium, or alloys thereof or polymers such as polyimide, polyetheretherketone (PEEK), polyamide, polyetherblockamide, polyethylene, polytetrafluoroethylene (PTFE), fluorinated ethylene propylene (FEP), and polyurethane. In an exemplary embodiment, transseptal guidewire 20 is manufactured from superelastic nitinol wire from Fort Wayne Metals in Fort Wayne, Ind.

In one embodiment, superelastic nitinol wire having a substantially circular cross-section is formed into elongate body 22a by a centerless grinding process. The superelastic nitinol wire, for example, may have a substantially uniform diameter and is threaded into a grinding machine to gradually decrease the diameter of the wire. Elongate body 22a may have a maximum diameter of about 0.015 inches at a proximal portion 21a which is tapered by centerless grinding to portion 24a. Portion 24a is sharpened to tapered distal section 28 terminating at pointed tip 29. Pointed tip 29 has a substantially circular cross-section and is positioned at the distal end of tapered distal section 28.

In another embodiment, elongate body 22a may have a maximum diameter of about 0.050 inches at a proximal portion 21a when used without an outer needle such as a Brockenbrough needle. In such an embodiment, portion 24a can be up to about 0.032 inches in diameter.

In an exemplary embodiment, after elongate body 22a is formed, radiopaque markers (25, FIG. 3) may be slidably coupled to portion 24a to form an imagable section (24, FIG. 3) of elongate body 22a. Imagable section (24, FIG. 3) has a substantially circular cross-section having a diameter of about 0.008 inches according to one embodiment. Thus, at least a portion of imagable section (24, FIG. 3) has a cross-sectional area smaller than the maximum cross-sectional area defined in portion 21a of elongate body 22a. In an exemplary embodiment, radiopaque markers (25, FIG. 3) coupled to portion 24a may be bands that have inner diameters greater than the diameter of portion 24a. Radiopaque marker bands, for example, may have inner diameters greater than about 0.008 inches and less than about 0.011 inches. Outer diameters of radiopaque marker bands may be greater than about 0.010 inches.

One or more radiopaque markers (25, FIG. 3) may be mounted to portion 24a of elongate body 22a by various coupling processes. Radiopaque markers, for example, may be mounted by adhesives, swaging, crimping, welding, or printing. Swaging techniques, for instance, include plastically deforming radiopaque markers (25, FIG. 3) using high pressure so that markers are crimped onto portion 24. Adhesive bonding methods may use low viscosity adhesives, such as cyanoacrylate, which is typically sold under trademarks like "Superglue" and "Krazy Glue." In an exemplary embodiment, platinum/10% iridium radiopaque marker bands (25, FIG. 3) using materials available from Johnson Matthey in West Chester, Pa. are attached to imagable section (24, FIG. 3) with wicking grade cyanoacrylate adhesive from Henkel Loctite Corporation in Rocky Hill, Conn. In another embodiment, radiopaque markers (25, FIG. 3) are slidably coupled to portion 24a without the use of adhesives or are otherwise applied.

FIGS. 4B and 4C illustrate enlarged views of tapered transitions from portion 21a of elongate body 22a to adjacent portion 24a and tapered distal section 28. Tapered transition from portion 21a to adjacent portion 24a may span a length of about 0.05 inches, for example, and taper from its maximum diameter to about 0.008 inches. As described above, portion 24a and pointed tip 29 are generally formed by centerless grinding such that portion 24a and pointed tip 29 have diameters less than the maximum diameter of elongate body 22a. Tapered distal section 28 has a portion with a diameter equal to or less than about 0.008 inches which tapers to a sharp pointed tip 29.

Referring now to FIGS. 4A and 5, additional aspects of a procedure for forming transseptal guidewire 20 are shown. In an exemplary embodiment, after radiopaque markers (25, FIG. 3) are coupled to imagable section 24 of elongate body 22a, at least a segment of portion 24a is ovalized or pressed using a mechanism such as a toggle press to form at least a portion of the end section 26. End section 26 is about ½ inch long and has a substantially non-circular cross-section distal of imagable section 24 and proximal of tapered distal section 28. As described in further detail below, when end section 26 is ovalized or otherwise pressed or formed, end section 26 has a first dimension (such as a width) in a direction transverse to longitudinal axis 1 that is larger than a second dimension (such as a thickness) in a second direction transverse to longitudinal axis 1. The first dimension of end section 26 is larger than the diameter of imagable section 24 to minimize the risk of radiopaque marker bands (25, FIG. 3) migrating from or falling off elongate body 22a.

The first dimension, for example, may have a width between about 0.008 and about 0.014 inches and greater than the inner and outer diameters of radiopaque marker bands (25, FIG. 3). Conversely, the inner diameters or dimension of radiopaque marker bands (25, FIG. 3) are preferably no larger than, and more preferably are smaller than, the first dimension of end section 26 such that the bands are restrained from passing over or along the end section 26. Also, the outer circumference of the bands preferably does not exceed the maximum circumference or perimeter of end section 26. When the outer circumference of the bands does not exceed the maximum circumference or perimeter of end section 26, then the bands are apt to pass more easily through an aperture in the septum formed by the end section 26. This reduces the interference as the transseptal guidewire is advanced.

Due to ovalization or pressing or other forming, the second dimension of end section 26 is smaller than the diameter of imagable section 24 and may have a thickness, for example, less than about 0.008 inches such as about 0.005 inches. Accordingly, end section 26 of the transseptal guidewire 20 is thinner and therefore more flexible than proximal portion 21a, imagable section 24, and tapered distal section 28 in a direction of curvature about an axis parallel to the first dimension. In other words, the end section 26, like an "I-beam," is more flexible in one direction (about an axis parallel to the first dimension) as compared to another direction (about an axis parallel to the second dimension).

Figure 6:
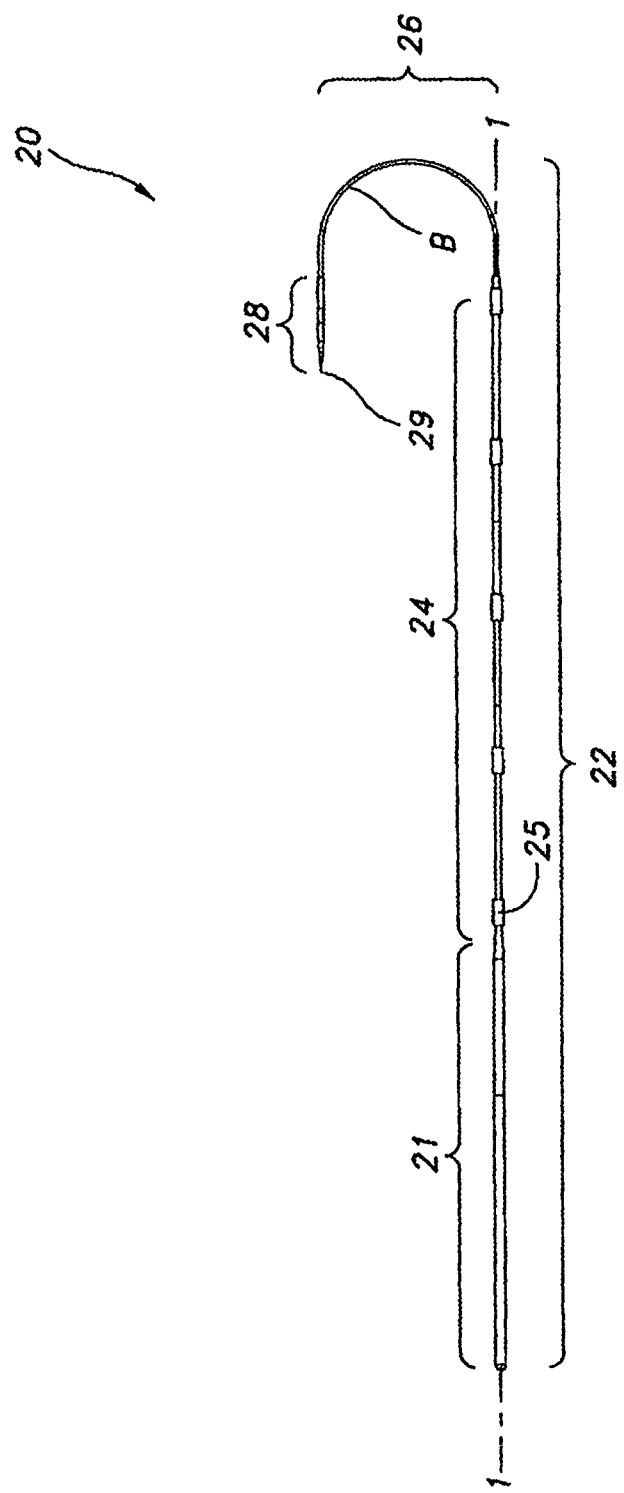
FIG. 6 is a side view of the transseptal guidewire illustrated in FIGS. 4A and 5 according to an exemplary method of fabricating the transseptal guidewire.

Referring now to FIGS. 5 and 6, end section 26 of transseptal guidewire 20 is biased to a curved configuration by a heat curving process or other forming process. For example, end section 26 may be treated at an elevated temperature, such as about 500 degrees Centigrade, for a set duration, such as about 10 seconds, to curve an otherwise linear superelastic nitinol wire. At least a portion of end section 26 is curved by a fixture and then cooled to retain the flexibility of the curved configuration. Thus, when end section 26 of transseptal guidewire 20 is not constrained within the lumen (13, FIG. 2) of outer needle (14, FIG. 2), end section 26 has an essentially non-traumatic conformation, such as a helical, curved, or hook shape.

For example, the radius "B" of the loop that forms the curved configuration can be about 0.125 inches or the diameter may be about 5-8 mm, though other dimensions are optionally selected. When the tapered distal section 28 is enclosed within the lumen (13, FIG. 2) of outer needle (14, FIG. 2), the entire length of the transseptal guidewire 20 is substantially straight and parallels longitudinal axis 1 of outer needle (14, FIG. 2).

Figure 7A:
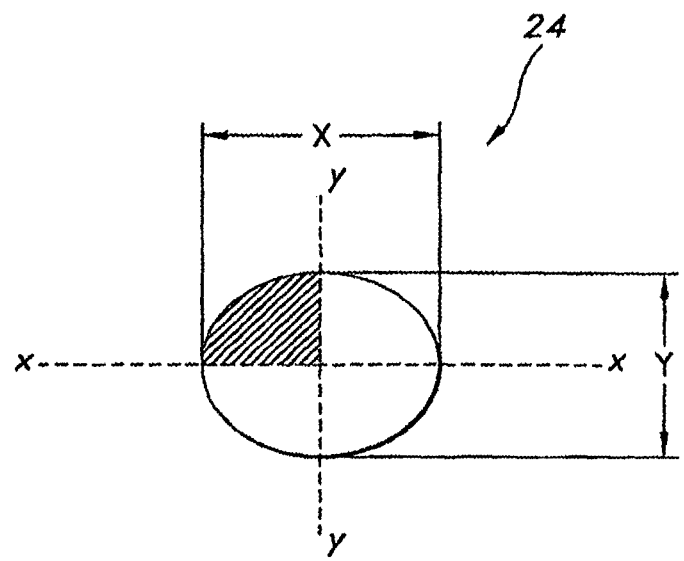
FIG. 7A is a cross-sectional view of an embodiment of an imagable section of the transseptal guidewire shown in FIG. 5 along lines 7A-7A.
Figure 7B:
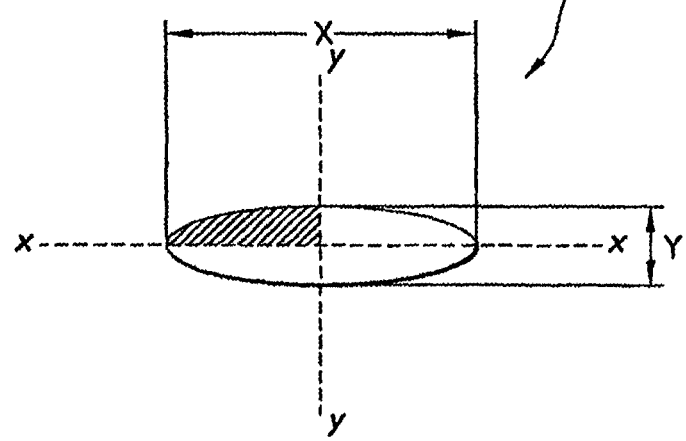
FIG. 7B is a cross-sectional view of an embodiment of an ovalized portion of an end section of the transseptal guidewire shown in FIG. 5 along lines 7B-7B.

FIGS. 7A and 7B illustrate cross-sectional views of transseptal guidewire 20 taken along lines A-A of imagable section 24 and lines B-B of end section 26 shown in FIG. 5. As shown in FIG. 7A, imagable section 24 has a substantially circular cross-section having a cross-sectional area less than the maximum cross-sectional area of elongate body (22, FIG. 6). In an exemplary embodiment, the diameter of imagable section 24 is less than the maximum diameter of elongate body (22, FIG. 6), preferably a diameter of about 0.008 in. When radiopaque marker bands (25, FIG. 6) are coupled to the imagable section 24, inner diameters of radiopaque marker bands (25, FIG. 6) are positioned adjacent the circumference or perimeter of imagable section 24.

As shown in FIGS. 5 and 7B, end section 26 is ovalized or pressed or otherwise formed from a portion (24a, FIG. 4a) of elongate body (22a, FIG. 4a) such that end section 26 has a substantially non-circular cross-section. End section 26 has a first dimension (such as a width) that is greater than the diameter of imagable section 24. As described above, and according to one exemplary embodiment, the first dimension X is between about 0.008 inch and about 0.014 inch, and is preferably about 0.011 inch. The second dimension Y of end section 26 is smaller than the diameter of imagable section 24 and may have a thickness less than about 0.008 inch, for example, about 0.005 inch. In an exemplary embodiment, radiopaque marker band (25, FIG. 6) has a circumference not exceeding the maximum circumference or perimeter of end section 26 such that radiopaque marker band (25, FIG. 6) can pass without substantial resistance through an aperture formed by the end section 26. Also, an inner dimension such as an inner diameter of the band is preferably smaller than the largest dimension of the end section 26 so that the band may be retained on imagable section 24 and not fall off the transseptal guidewire 20 by passing through or along end section 26. Radiopaque marker bands (25, FIG. 6) may have a pull force greater or equal to about 3 Newtons in compliance with ISO 11070, thereby securing the bands to imagable section 24.

Figure 8:
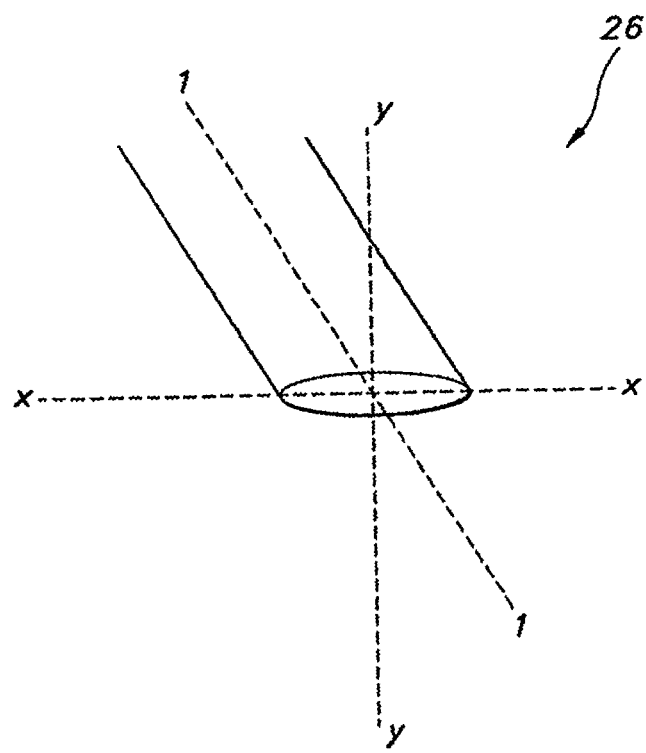
FIG. 8 is a perspective cross-sectional view of an embodiment of the end section of the transseptal guidewire.

Referring now to FIGS. 7B and 8, when end section 26 is ovalized according to the illustrated embodiment, first dimension X of end section 26 is formed in a first direction transverse to longitudinal axis 1 of elongate body (22, FIG. 5) and second dimension Y is formed in a second direction transverse to longitudinal axis 1. First dimension X is larger than second dimension Y, thus end section 26 is thinner in thickness and more flexible in at least one direction as compared to proximal portion 21, imagable section 24, and tapered distal portion 28 of transseptal guidewire 20.

The exemplary embodiments of end section 26 are illustrated schematically as having a portion with a cross-sectional shape that is like an oval. This oval shape may be formed by pressing or other techniques. It is contemplated that this shape may be something other than an oval as well, while still maintaining first and second respective dimensions. For example, the shape may be flattened or somewhat rectangular. It may also take any other geometric shape. In any shape selected, however, the subject portion of end section 26 preferably serves at least one of the functions of retaining radiopaque bands, promoting increased flexibility in at least one direction, and providing an outer perimeter close to the outer perimeter of the radiopaque bands.

Figure 9:
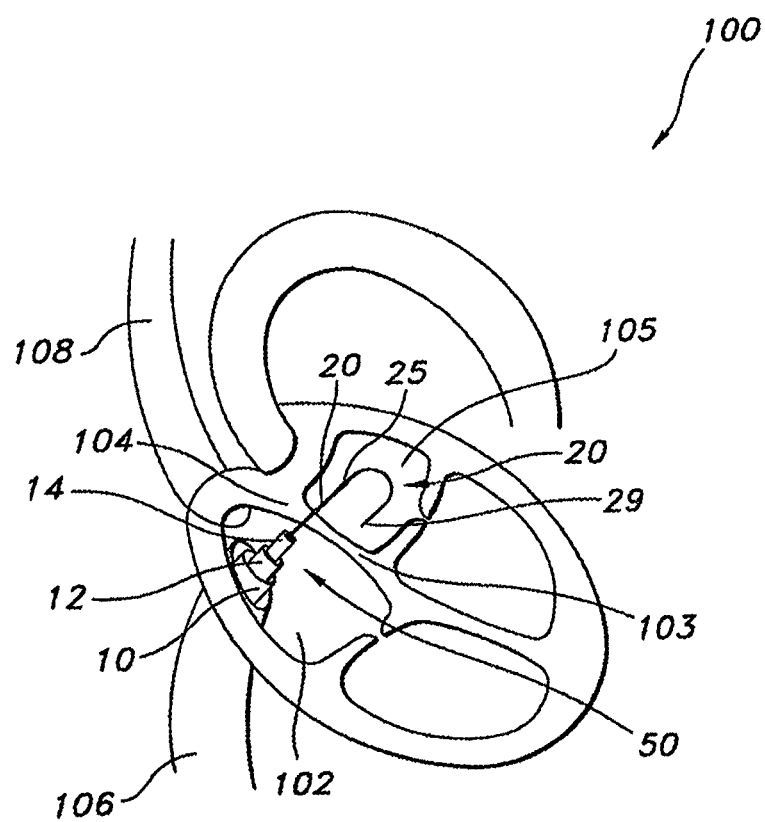
FIG. 9 is a schematic representation of the heart showing vascular access of the transseptal guidewire to the left atrium.

Referring now to FIGS. 1, 2, 6, and 9, methods of perforating an intra-atrial septum 104 and confirming traversal of the intra-atrial septum 104 to treat, for example, patent foramen ovale (PFO) or to gain access to the left atrium 105 are illustrated. As shown in FIGS. 1 and 9, one exemplary method includes the step of introducing an intravascular sheath 10 in a vessel such as the inferior vena cava 106 or superior vena cava 108 to access the chamber of right atrium 102. In an embodiment, the distal end of sheath 10 is tapered to enhance advancement of the sheath 10 though the intra-atrial septum 104 after perforating intra-atrial septum 104.

Referring to FIG. 1, after the sheath 10 is properly positioned in the right atrium 102, dilator 12 and outer needle 14 of transseptal trocar device 50 are advanced distally toward the intra-atrial septum 104. The distal end of outer needle 14 is positioned against fossa ovalis 103 at the perforate site and pushed against fossa ovalis 103 until some tenting of the fossa ovalis 103 is caused. The tenting should be sufficient to correctly identify, preferably by fluoroscopic visualization, the perforate site in the intra-atrial septum 104. Alternatively, visualization techniques such as intracardiac echocardiography (ICE) or magnetic resonance imaging (MRI) can be used that may work without tenting.

Once outer needle 14 is positioned, transseptal guidewire 20 is advanced relative to the outer needle 14 through the septum 104. The perforation force of transseptal guidewire 20 is less than or equal to the perforation force of currently available transseptal needles such as a Brockenbrough needle. According to one embodiment, at its most distal position, about 10 mm of the transseptal guidewire 20 should extend from the distal end of outer needle 14. Alternatively, the most distal position could be extended about 30 mm to 50 mm, e.g., 3-5 cm, if end section 26 of transseptal guidewire 20 has a hook shape, as is shown in FIG. 6. Thus, after perforation of fossa ovalis 103, a portion of transseptal guidewire 20 may be extended into left atrium 105 to confirm that it is in the left atrium 105. In another embodiment, curved portion of transseptal guidewire 20 may be advanced such that the curved portion enters one of the pulmonary veins (not shown) in the left atrium 105.

In an embodiment of this procedure, as elongate body 22 is advanced through outer needle 14, the straight configuration of transseptal guidewire 20 shown in FIG. 2, transitions to curved configuration of end section 26. A portion of end section 26 extends into the left atrium 105 such that pointed tip 29 of the tapered distal section 28 curves back toward the intra-atrial septum 104 as shown in FIG. 9. Imagable section 24 proximal of end section 26 may then be advanced into the left atrium 105 and imaged by means of at least one radiopaque marker 25 coupled to the imagable section 24. Radiopaque markers 25 may be restricted from movement along longitudinal axis 1 of the transseptal guidewire 20 and exclusively positioned along imagable section 24 by ovalizing or otherwise pressing or forming end section 26 as shown in FIG. 7B or otherwise changing the cross-sectional shape of the end section 26. When radiopaque markers 25 are positioned within the left atrium 105, traversal of the intra-atrial septum 104 and the location of transseptal guidewire 20 are confirmed by imaging of radiopaque markers 25.

In an embodiment of this procedure, outer needle 14 follows the path of transseptal guidewire 20 through the septum 104. Alternatively, because of the added stiffness provided by outer needle 14, transseptal guidewire 20, dilator 12, and sheath 10 can be advanced through septum 104. The motion of the transseptal guidewire 20 may be forward, vibrating, reciprocating, linear, or rotational, for example. In one embodiment, movement of the transseptal guidewire 20 is accomplished manually, thus providing easier manipulation for the physician.

As shown in FIGS. 1 and 9, once the pointed tip 29 of the transseptal guidewire 20 is positioned within the septum 104, fossa ovalis 103 tissue provides support to the transseptal guidewire 20 until sheath 10, dilator 12, and/or outer needle 14 is delivered into the left atrium 105. According to standard catheterization procedures, once sheath 10 and/or dilator 12 is positioned in the left atrium 105, other components of the transseptal trocar device 50, for example, the transseptal guidewire 20, outer needle 14, and dilator 12 can be retracted and the sheath 10 can be used to deliver implants, for example, such as an atrial occluder for the treatment of a patent foramen ovale, electrophysiology catheters, or other intracardiac therapeutic devices. In an embodiment of this procedure, the transseptal guidewire 20 is left in the left atrium 105 to maintain the perforate site as well as to image the operative area by radiopaque markers 25, or to act as a guidewire for delivery of over-the-wire devices into the left atrium. In another embodiment, the transseptal guidewire 20 is withdrawn, e.g., into the outer needle 14.

The method for transseptal perforation using the transseptal device described herein offers several significant advantages. For example, when using the devices and methods according to exemplary embodiments of the invention, inadvertent contact of the transseptal guidewire 20 with the left atrial free wall immediately after the septum 104 is perforated does not result in damage to or perforation of the left atrial free wall because the end section 26 of the transseptal guidewire 20 is flexible and/or biased to a curved configuration when fully extended from the distal end of outer needle 14. In other words, the flexibility and/or curvature of the end section renders it atraumatic.

When the end section 26 of the transseptal guidewire 20 contacts the left atrial free wall or pulmonary vein, for example, end section 26 of transseptal guidewire 20 harmlessly bends rather than perforates the left atrial free wall. In one embodiment, the end section 26 of the transseptal guidewire 20 bends because of the enhanced flexibility of the ovalized end section 26, as described above. In an embodiment, perforation of the left atrial wall is avoided by modifying the shape of the end section 26 of transseptal guidewire 20 to form, for example, a hook or a bend. In yet another embodiment, end section 26 of transseptal guidewire 20 may be advanced into one of the pulmonary veins in the left atrium 105 and straightened by advancing a transseptal introducer, such as dilator 12 or sheath 10, over end section 26.

Another advantage of the transseptal trocar device embodiments described herein is the ability of the device to perforate through thick septum such as septum secundum. The transseptal trocar devices according to the invention can also be used for remote suturing of a patent foramen ovale or other defects that may be accessed vascularly. This is possible, for example, because the fit between the outer needle 14 and the guidewire 20, especially when provided with an ovalized end section, promotes the column strength of the guidewire and reduces the bending or buckling tendency of the guidewire. This fit, promoted by the ovalized end section, improves the ability of the guidewire to perforate tougher tissue yet, when extended from the end of the needle 14, becomes relatively atraumatic.

In an exemplary embodiment, the pointed tip of the guidewire 20 is significantly sharper and/or smaller than the tip of the transseptal outer needle 14. Thus, the guidewire 20 is able to perforate through the fossa ovalis 103 with less force. When needle 14 punctures the fossa ovalis 103, the needle 14 continues on a path towards the lateral wall of the left atrium. According to exemplary embodiments described herein, however, when the guidewire 20 is extended from the tip of the transseptal outer needle 14, guidewire 20 prevents the needle 14 from puncturing the lateral wall of the left atrium.

By way of example, the flexible members are manufactured using nickel-titanium material, such as superelastic nitinol, or other shape memory alloy materials. The nickel-titanium wire, when properly manufactured, exhibits elastic properties for the wire to be manipulated (e.g., bent) by an operator and then returned to substantially the same shape the wire possessed prior to it being manipulated. Thus, transseptal guidewire 20 does not kink or buckle during use with transseptal trocar device 50.

In an exemplary embodiment, components of transseptal trocar device 50 are passed through a straightener and optional hemostatic Y adapter (not shown) without resistance. The hemostatic Y adapter may be used to supply contrast imaging fluid through the sheath 10, dilator, and/or needle 14. Alternatively, the Y adapter may be coupled to a pressure monitor to measure atrial pressure change when the intra-atrial septum 104 is perforated.

In yet another embodiment, transseptal trocar device 50 may be provided in a sterilized kit which includes intravascular sheath 10, dilator 12, outer needle 14, transseptal guidewire 20, and the hemostatic Y valve. The components of the kit may be packaged in a tyvek/polymylar pouch for one time use such that the transseptal trocar device 50 may be disposable after a surgical procedure. Additional aspects of the Y adapter and transseptal catheterization methods are described in U.S. Pat. No. 5,312,341, U.S. Patent Publication 2006/0064062, and U.S. Patent Publication 2005/0101984, which are incorporated herein fully by reference.

FIGS. 10-17 illustrate another embodiment of a transseptal guidewire 220 according to an exemplary aspect of the invention. Transseptal guidewire 220 is similar to the guidewire 20 described above in connection with FIGS. 1-9, but differs in that the transseptal guidewire 220 is configured in such a way as to prevent the perforating tip 229 of the transseptal guidewire 220 from catching, or reduce the risk of catching, on the inside of a component of a transseptal access system, such as a needle or dilator, as the transseptal guidewire 220 is advanced distally through the transseptal access system.

For example, a transseptal needle or a transseptal dilator may define a lumen that is reduced in size from a first diameter in a proximal section to a second diameter at the distal opening that is smaller than the first diameter. There may also be a transition step between the first and second diameters. It is therefore advantageous to reduce the occasion that the perforating tip would contact such a transition step or diameter reduction as the transseptal guidewire is advanced distally through or into the transseptal needle or dilator or other such component. Referring generally to FIGS. 10-17, the transseptal guidewire 220 is illustrated. The transseptal guidewire 220 is configured to perforate the intra-atrial septum and has an elongated body 222, an end section 226 biased in a curved configuration to define a proximal curve 226a, and a distal section 228 biased in a curved configuration to define a distal curve 228a, the distal curve 228a being oriented in a direction generally opposite that of the proximal curve 226a.

A system configured to perforate the intra-atrial septum is also illustrated. A transseptal access system such as a system including a dilator 212 (FIG. 16) or a transseptal needle 214 (FIG. 15) or a combination thereof (similar to dilator 12 (FIG. 2), transseptal needle 14 (FIG. 2), or a combination of a dilator and a transseptal needle (FIG. 2)) includes a wall 232, 235 defining a lumen 213, 215 extending from a proximal section 230, 216 to a distal opening 231, 217. The lumen 213, 215 is reduced in size from a first diameter in the proximal section 230, 216 to a second diameter at the distal opening 231, 217 that is smaller than the first diameter. A transseptal guidewire 220 is configured to be inserted into the lumen 213, 215 of the transseptal access system 212, 214. The transseptal guidewire 220 has a distal section 228 with a longitudinal axis 1a and a perforating tip 229 laterally offset from the longitudinal axis 1a. The perforating tip 229 of the transseptal guidewire 220 is configured to be offset from the wall 232, 235 of the transseptal access system 212, 214 a distance that is equal to or smaller than the second diameter of the lumen 213, 215 of the transseptal access system 212, 214, thereby reducing or avoiding contact between the perforating tip 229 of the transseptal guidewire 220 and the wall 232, 235 as the perforating tip 229 is advanced distally through the distal opening 231, 217 of the transseptal access system 212, 214.

In another embodiment, the transseptal access system 212a, 214, 250 (such as for example a dilator 12 (FIG. 2), a transseptal needle 14 (FIG. 2), or a combination of a dilator and a transseptal needle (FIG. 2)) includes a wall 232a, 235 defining a lumen 213a, 215 that has a first section 233, 216 with a first diameter and a second section 234, 217 with a second diameter smaller than the first diameter. A transition step 219, 218 is defined between the first and second sections. A transseptal guidewire 220 is configured to be inserted within the lumen 213a, 215 of the transseptal access system 212a, 214, 250. The transseptal guidewire 220 has an elongated body and a distal section 228. The distal section 228 has a longitudinal axis 1a and a perforating tip 229 laterally offset from the longitudinal axis 1a. The perforating tip 229 of the transseptal guidewire 220 is configured to be offset from the wall 232a, 235 of the transseptal access system 212a, 214, 250 a distance that is equal to or larger than the transition step 219, 218 defined between the first and second sections of the lumen 213a, 215, but equal to or smaller than the sum of the transition step 219, 218 and the second diameter. Thus, contact between the perforating tip 229 and the transition step 219, 218 is reduced or minimized as the perforating tip 229 is advanced through the lumen 213a, 215 from the first section 233, 216 to the second section 234, 217 of the lumen 213a, 215.

In yet another embodiment, a transseptal guidewire 220 is configured to be inserted within the lumen 213a, 215 of a transseptal access system 212a, 214, 250 (such as for example a dilator 12 (FIG. 2), a transseptal needle 14 (FIG. 2), or a combination of a dilator and a transseptal needle (FIG. 2)). The transseptal access system 212a, 214, 250 defines a lumen 213a, 215, the lumen 213a, 215 having a first section 233, 216 with a first diameter, a second section 234, 217 with a second diameter smaller than the first diameter, and a transition step 219, 218 defined between the first section 233, 216 and second section 234, 217. The transseptal guidewire 220 is configured to be inserted within the lumen 213a, 215 of the transseptal access system 212a, 214, 250. The transseptal guidewire 220 has an elongated body 222, an end section 226 biased in a curved configuration to define a proximal curve 226a, a distal section 228 biased in a curved configuration to define a distal curve 228a, and a distal perforating tip 229. The distal curve 228a is oriented in a direction generally opposite that of the proximal curve 226a, thereby avoiding or reducing a tendency for contact between the perforating tip 229 and the transition step 219, 218 as the perforating tip 229 is advanced through the lumen 213a, 215 from the first section 233, 217 to the second section 234, 217 of the lumen 213a, 215.

In yet another embodiment, the transseptal access system 212a, 214, 250 defines a lumen 213a, 215, the lumen 213a, 215 having a first section 216, 233 with a first diameter, a second section 217, 234 with a second diameter smaller than the first diameter, and a transition step 218, 219 defined between the first section 216, 233 and second section 217, 234. A transseptal guidewire is 220 configured to be inserted within the lumen 213a, 215 of the transseptal access system 212a, 214, 250 and has an elongated body 222, a perforating tip 229, and means for reducing (or avoiding or minimizing) contact between the perforating tip 229 and the transition step 218, 219 as the perforating tip 229 is advanced through the lumen 213a, 215 from the first section 216, 233 to the second section 217, 234 of the lumen 213a, 215.

The means for reducing contact between the perforating tip 229 and the transition step 218, 219 preferably offsets the perforating tip 229 from an axis 1a of the elongated body 222 of the transseptal guidewire 220. The reducing means is optionally a curve, a bend, or an angle formed in a distal section 228 of the transseptal guidewire 220.

A method of perforating the intra-atrial septum is also provided. The method includes introducing a transseptal guidewire 220 toward the intra-atrial septum. A transseptal guidewire 220 is constrained within a lumen 213a, 215 of the transseptal access system 214, 250 such that a proximal curve 226a defined in an end section 226 of the transseptal guidewire 220 and a distal curve 228a defined in a distal section 228 of the transseptal guidewire 220 are oriented in generally opposite directions. The transseptal guidewire 220 is then advanced from a first section 233, 216 of the lumen 213a, 215 having a first diameter to a second section 234, 217 of the lumen 213a, 215 having a second diameter smaller than the first diameter, while avoiding contact between a perforating tip 229 of the transseptal guidewire 220 and a transition step 219, 218 defined between the first section 233, 216 and second section 234, 217 of the lumen 213a, 215.

In yet another embodiment, a method of forming a transseptal guidewire 220 configured to perforate the intra-atrial septum is provided. The method includes forming a proximal curve 226a in an end section 226 of an elongated body 222 such that it is biased in a curved configuration. A distal curve 228a is formed in a distal section 228 of the elongated body 222 such that the distal curve 228a is biased in a curved configuration and oriented in a direction generally opposite that of the proximal curve 226a.

Figure 10:
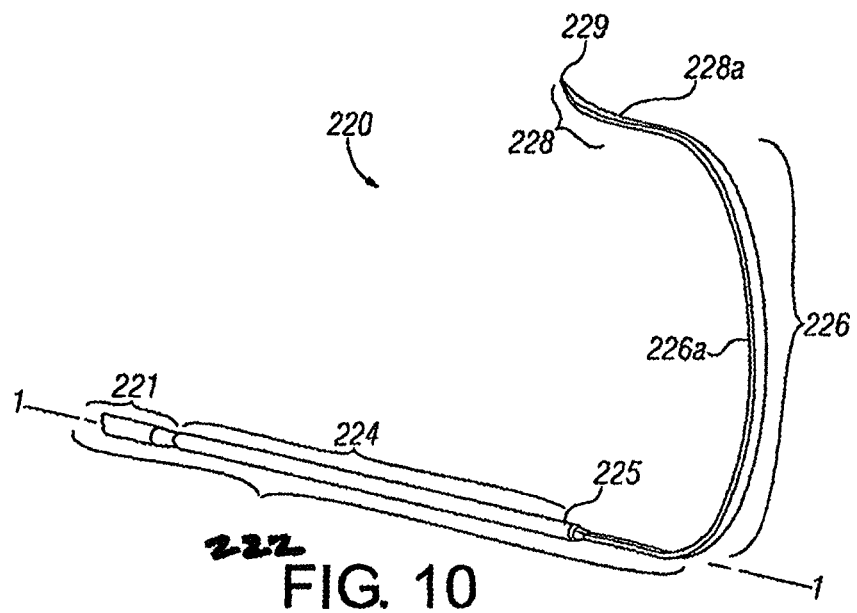
FIG. 10 is a perspective view of a transseptal guidewire according to a another exemplary embodiment of the invention.

Referring now to the figures in detail, FIG. 10 illustrates a transseptal guidewire 220 according to an exemplary embodiment. The transseptal guidewire 220 includes an elongate body 222, an end section 226, and a distal section 228. The end section 226 is biased in a curved configuration to define a proximal curve 226a, such as a J-shaped curve. In the illustrated embodiment of transseptal guidewire 220, the proximal curve extends a distance and over an angle sufficient that a longitudinal axis 1a (FIG. 12) of a straight portion of the distal section 228 is substantially parallel to the longitudinal axis 1 of the elongate body 222 of the transseptal guidewire 220, though greater and lesser curves are also contemplated.

The distal section 228 is biased in a second curved configuration to define a distal curve 228a such that the perforating tip 229 of the transseptal guidewire 220 is offset from the longitudinal axis 1a. As will be described in detail below, the distal curve 228a is oriented in a direction generally opposite that of the proximal curve 226a to minimize contact of the perforating tip 229 against a surface of a lumen of a device, such as a transition step or taper or diameter change of a transseptal access system, through which the transseptal guidewire 220 is introduced.

According to an exemplary embodiment, the end section 226 of the transseptal guidewire 220 is ovalized such that the end section 226 has a substantially non-circular cross section. As described above and shown in FIG. 7B, ovalizing end section 226 partly assists with biasing the end section 226 in a curved configuration to form the proximal curve 226a. When the end section 226 is ovalized or otherwise pressed, flattened, or formed, the end section 226 has a first dimension (such as a width) in a direction transverse to longitudinal axis 1 that is larger than a second dimension (such as a thickness) in a second direction transverse to longitudinal axis 1.

According to an exemplary embodiment, the distal section 228 of the transseptal guidewire 220 is also ovalized, thereby assisting with biasing the distal section 228 in a second curved configuration to form the distal curve 228a. In one embodiment, the distal curve 228a is formed by a bend or an angle in the distal section 228. Whether or not the distal section 228 is ovalized, the perforating tip 229 may be tapered or otherwise formed to a sharp perforating point.

As also illustrated in FIG. 10, the elongated body 222 of the transseptal guidewire 220 has a portion 224 proximal of end section 226. Portion 224 has a substantially circular cross section relative to the end section 226. In one embodiment, portion 224 is an imagable section having a radiopaque marker such as a coil 225 coupled to the imagable section 224. The radiopaque coil 225 is resiliently compressible in at least the direction of the longitudinal axis 1 so it may be atraumatic when advanced from the right atrium into the left atrium after the intra-atrial septum has been punctured. According to an exemplary embodiment, the radiopaque coil 225 has a pull force to withstand a minimum tensile force of at least about 0.67 lbs (approximately 3N).

According to an exemplary embodiment, the radiopaque coil 225 may be made of a platinum/tungsten alloy, for example, and is sufficiently visible under fluoroscopy (x-ray) to assist with imaging of the operative area. For example, the radiopaque coil may be 92% platinum and 8% tungsten. Other radiopaque materials may also be used such as palladium, palladium alloy, iridium, gold, tungsten, etc., or any radiopaque material that can be coiled or otherwise configured to be coupled to the transseptal guidewire 220.

Figure 11A:
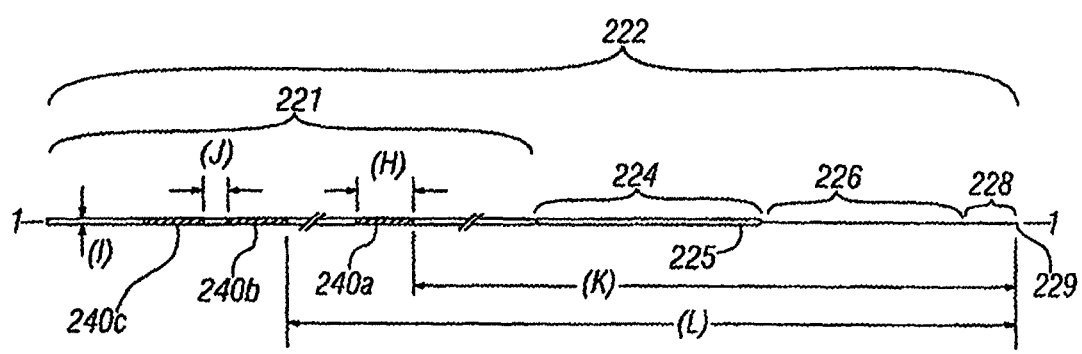
FIG. 11A is a side view of the transseptal guidewire illustrated in FIG. 10 according to an exemplary method of fabricating the transseptal guidewire.
Figure 11B:
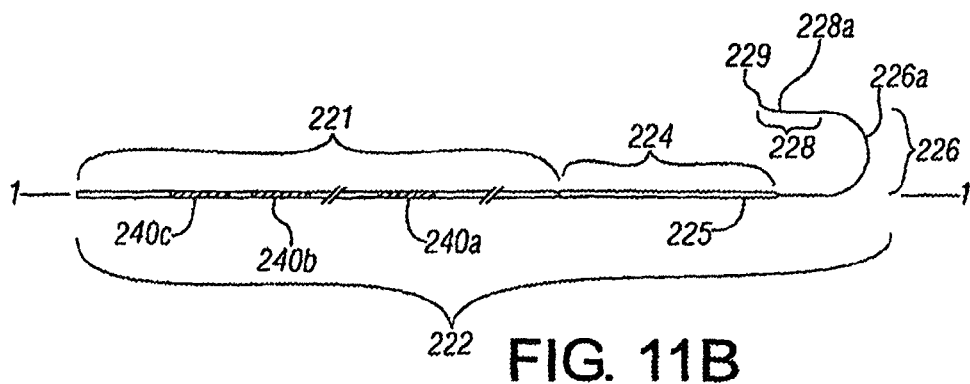
FIG. 11B is a side view of the transseptal guidewire illustrated in FIG. 11A according to an exemplary method of fabricating the transseptal guidewire.

Additionally, a portion 221 of the elongated body 222 proximal to the imagable section 224 includes a tapered transition to imagable section 224. According to an exemplary embodiment, the radiopaque coil 225 is positioned adjacent the tapered transition and then held in place by crimping a portion of the end section 226 opposite the tapered transition. Because portion 221 has a diameter that is generally equal to or greater than the diameter of the imagable section 224, the radiopaque coil 225 is thus constrained on the imageable section 224. For example, portion 221 may have a diameter of about 0.015 inch and the imagable section 224 may have a diameter of about 0.008 inch. Thus, the larger diameter of portion 221 constrains the radiopaque coil 225 to the imagable section 224 between the adjacent portion 221 and the ovalized end section 226. Referring now to FIGS. 11A-11B, side views of the transseptal guidewire 220 are illustrated. In one exemplary embodiment shown in FIG. 11A, before the transseptal guidewire 220 is provided with the curves 226a, 228a, or when the transseptal guidewire 220 is maintained in a constrained condition (such as when the guidewire 220 is positioned within a lumen of a transseptal access system), the guidewire 220 has a substantially straight configuration. Thus, in the pre-curved or constrained condition, the portion of the transseptal guidewire 220 that forms the proximal curve 226a and the distal curve 228a occupy substantially the same longitudinal axis 1.

Figure 12:
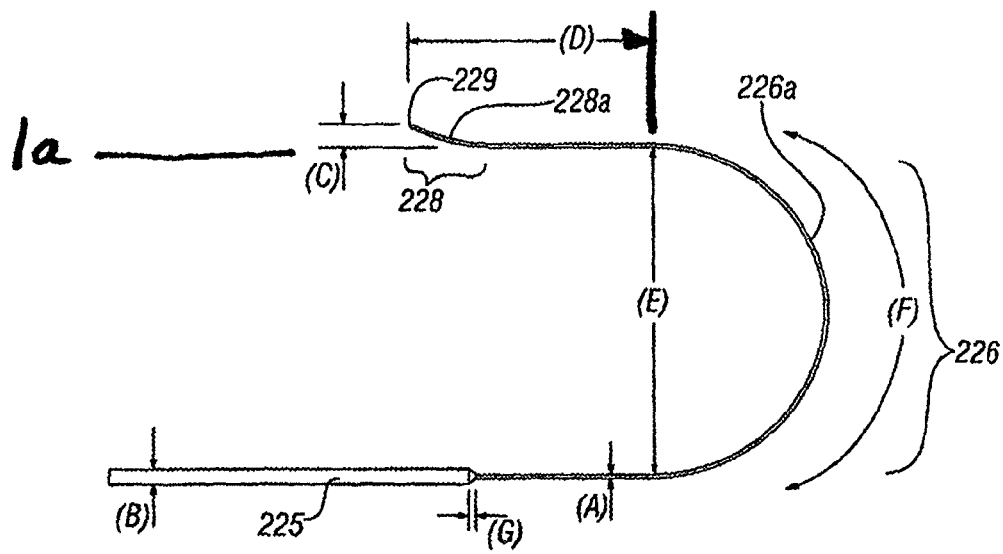
FIG. 12 is an enlarged view of a distal portion of the transseptal guidewire shown in FIG. 11B.

When the transseptal guidewire 220 is in an unconstrained or relaxed configuration, shown in FIGS. 11B and 12, the proximal curve 226a and the distal curve 228a preferably occupy the same plane. In another embodiment, however, the proximal curve 226a and the distal curve 228a optionally occupy respective planes that are angled with respect to each other.

Referring to FIG. 11A, the linear length of the distal section 228 and end section 226 (i.e., from the perforating tip 229 to the beginning of the radiopaque coil 225) may be about 2 cm, although larger and smaller dimensions are contemplated. The total length of the elongate body 222 of the transseptal guidewire 220 from the perforating tip 229 to the opposite end may be about 120 cm. It is contemplated, however, that the elongate body 222 may be any length to accommodate different patients or different procedures. For example, a pediatric transseptal guidewire 220 configured for use with children may have a shorter length compared to a transseptal guidewire 220 configured for use with adults.

According to an exemplary embodiment, the transseptal guidewire 220 includes printed markers 240a-c that may be used to indicate the length of the transseptal guidewire 220 at a specific location of the elongate body 222. For example, the distance [K] from the perforating tip 229 to the first printed marker 240a may be about 70 cm, and about 71.7 cm with a tolerance of +/−5.0 mm according to one exemplary embodiment. Also, the distance [L] from the perforating tip 229 to the second printed marker 240b may be about 80 cm, or about 78.5 cm with a tolerance of +/−5.0 mm according to one exemplary embodiment. It is contemplated that other marker distances may also be used to allow a physician to ascertain the insertion depth of the transseptal guidewire 220 when used in a patient. For instance, after advancing a portion of the transseptal guidewire 220 into a patient, the physician may be able to use the markers 240a-c to determine how much farther to advance the guidewire 220 to the operative site.

According to an exemplary embodiment, the printed marker bands 240a-c may have a width [H] of about 5 mm with a tolerance of +/−1 mm. Additionally, the printed marker bands 240a-c may be spaced at a distance [J] of about 2 mm from each other. It is also contemplated that the optional printed or otherwise applied marker bands 240a-c may be any width [H] and spaced at any spacing distance [J] from each other so long as they allow a physician to ascertain the length of the transseptal guidewire 220 at specific location of the elongate body 222, as described above.

According to another exemplary embodiment, the printed markers 240a-c may be attached to the transseptal guidewire 220 by pad printing to the portion 221 of the elongate body 222 proximal of the imageable section 224. When the printed markers 240a-c are attached to the transseptal guidewire 220, the printed marker diameter may be about 0.0005 inch larger than the maximum diameter [I] of the elongate body 222. According to an exemplary embodiment, the maximum diameter [I] of the elongate body 222 depends on the use of the transseptal guidewire 220. For example, for a transseptal guidewire 220 used in conjunction with a dilator (see, e.g., dilator 12, FIG. 2) the maximum diameter of the elongated body 222 may be about 0.050 inch. For a transseptal guidewire 220 used in conjunction with an outer needle (see, e.g., needle 14, FIG. 2), the maximum diameter [I] of the elongated body 222 may be about 0.015 inch. It is contemplated that other diameters [I] may be selected in order to configure the transseptal guidewire 220 for use with various components and procedures (e.g., so that the transseptal guidewire 220 may be introduced or contained within the lumen of the dilator (12, FIG. 2) or outer needle (14, FIG. 2) or any other component, or so that the transseptal guidewire 220 can be used independent of other components).

As illustrated in FIG. 11B, in the unsupported or relaxed condition, the proximal curve 226a of the transseptal guidewire 220 flexes or reverts into an atraumatic configuration such as a J-shape. Thus, the perforating tip 229 is rendered atraumatic or less prone to puncturing or damaging tissue inadvertently. Furthermore, it is contemplated that the second curve (e.g., the distal curve 228a and the resulting S-shape of the guidewire's distal portion) reduces the depth of penetration of the perforating tip 229, thereby further rendering the transseptal guidewire 220 less traumatic in the unsupported condition.

According to an exemplary embodiment, at least a portion of the end section 226 of an elongate body 222 may be heat treated, such as by a heat curving process, to a provide the flexible curved configuration of the proximal curve 226a. The distal section 228 of the elongate body 222 is also heat curved to provide the distal curve 228a, thus providing a configuration in which the perforating tip 229 is offset from a longitudinal axis 1a of the distal section 228. Due to the perforating tip 229 offset, the depth of penetration when the transseptal guidewire 220 is in the constrained condition is preferably less than the length of the distal curve 228a. Additional aspects of the proximal curve 226a and distal curve 228a are described in further detail below.

Referring now to FIG. 12, an enlarged view of the end section 226 and distal section 228 is illustrated. According to an exemplary embodiment, the distal curve 226a is formed by an arcuate or bent or angled portion of the distal section 226. The distal section 226, for example, may be heat curved or bent so that the curve diameter [E] of the proximal curve 226a is about 8 mm with a +/−1 mm tolerance, for example. It is contemplated that the curve diameter [E] may be more or less than 8 mm to accommodate adult and pediatric or other uses of transseptal guidewire 220.

According to an exemplary embodiment, the arc curvature [F] of the proximal curve 226a is generally about 180 degrees for both an adult or pediatric system. However, the arc curvature [F] may be more or less than 180 degrees depending on the desired relaxed atraumatic configuration. For example, a proximal curve 226a with a larger arc curvature is generally less atraumatic in the unconstrained condition than a curve with a lower arc length. It is also contemplated that the arc curvature [F] may be selected from any such arc curvature to reduce the risk that the transseptal guidewire 220 might catch on the inside of a needle (214, FIG. 15) or dilator (212, FIG. 16) or other component, as will be described in detail below.

As illustrated in FIG. 12, the end section 226 has a length greater than the distal section 228. Thus, the arc length of the proximal curve 226a is generally larger than the arc length of the distal curve 228a to provide sufficient curvature in the atraumatic configuration. A tip extension [D] extends distal of the proximal curve 226a at a length about 5.5 mm with a tolerance of +/−1 mm to the perforating tip 229, for example. However, the tip extension [D] may be greater or less than 5.5 mm for the transseptal guidewire 220 to remain atraumatic in the relaxed configuration. It is also contemplated that even if the tip extension [D] is 0 mm, the transseptal guidewire 220 will still function and remain atraumatic in the relaxed configuration.

According to an exemplary embodiment, in order to enhance the atraumatic characteristics of the transseptal guidewire 220, and also to prevent or reduce any tendency of the perforating tip 229 to catch in the lumen of a transseptal needle or dilator or other component, the perforating tip 229 may be offset from the longitudinal axis 1a of a straight portion of the tip extension [D]. For an adult system, the perforating tip 229 may be offset by a distance [C], measured in a direction perpendicular to the longitudinal axis 1a, from about 0.01 to about 0.05 inch, but preferably at a distance of about 0.03 inch. For a pediatric system, the perforating tip 229 may be offset from the longitudinal axis 1a at a distance [C] from about 0.005 to about 0.03 inch, but preferably at a distance of about 0.02 inch. It is contemplated that other offset distances [C] may be selected to prevent the perforating tip 229 from catching on the inside of a component such as a transseptal needle or dilator, which components may include a transition step or a diameter reduction, as will be described in further detail below.

Referring now to FIGS. 7B, 10, and 12, according to the illustrated embodiment, the ovalized or flattened portion of the end section 226 is generally about 0.75 inch long. The end section 226, however, may be any length sufficient to provide the proximal curve 226a. The thickness [A] of the ovalized portion may be configured to be between about 0.008 and about 0.014 inch, but preferably about 0.012 inch. Other thicknesses may also be used to allow the end section to be biased in the curved configuration.

As described above with reference to FIG. 7B, the first dimension X of end section 226 is formed in a first direction transverse to longitudinal axis 1 of elongate body (222, FIG. 10) and second dimension Y is formed in a second direction transverse to longitudinal axis 1. First dimension X is larger than second dimension Y, thus end section 226 is thinner in thickness [A] and more flexible in at least one direction as compared to proximal portion 221 and imagable section 224 of the transseptal guidewire 220.

Figure 13:
FIG. 13 is a plan view of a template used according to an exemplary method of fabricating the transseptal guidewire.
Figure 14:
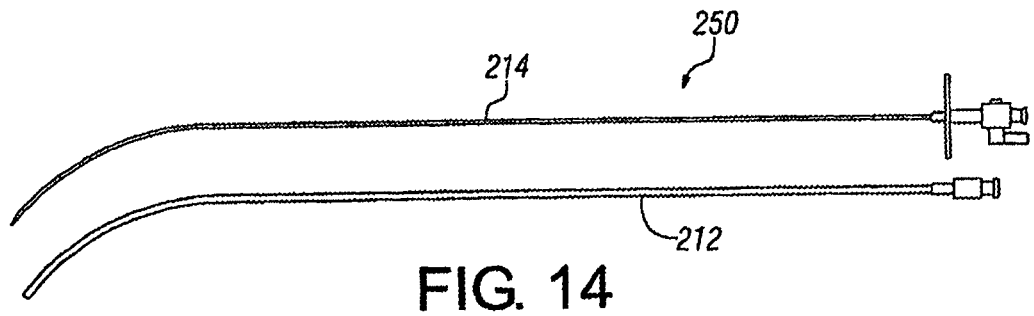
FIG. 14 is a side view of components of the transseptal trocar device shown in FIG. 2.

Referring now to FIG. 13, a method of confirming the dimensions of a transseptal guidewire 220 is illustrated. The template illustrated in FIG. 13 permits visual inspection of a guidewire 220 to confirm that the curved configuration of the distal portion is within a specified tolerance. In use, the template is placed on a flat surface and the transseptal guidewire 220 is positioned over the template. The distal portion of the transseptal guidewire 220 is aligned to the "ALIGN HERE" position. The position of the perforating tip 229 of the transseptal guidewire 220 is then compared to the rectangular target formed on the template. If the perforating tip 229 of the transseptal guidewire 220 falls within the rectangular target, then the curved end of the transseptal guidewire 220 has been manufactured appropriately and would pass this aspect of inspection. If the perforating tip 229 of the transseptal guidewire 220 falls outside the rectangular target, then the curved end of the transseptal guidewire 220 has been manufactured inappropriately and would fail this aspect of inspection.

Figure 15:
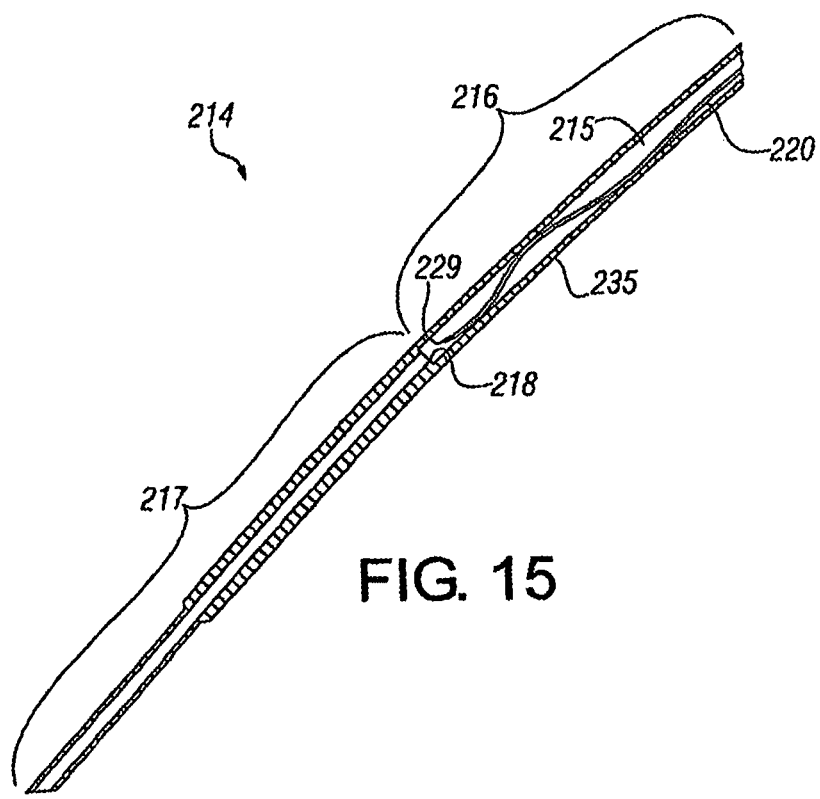
FIG. 15 is a cross-sectional side view of the transseptal guidewire shown in FIG. 10 being constrained within a transseptal needle.
Figure 16:
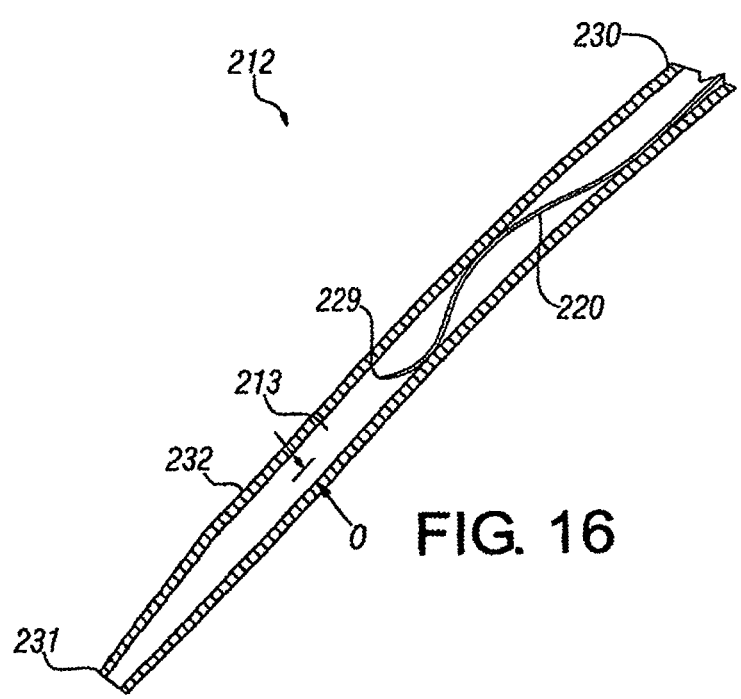
FIG. 16 is a cross-sectional side view of the transseptal guidewire shown in FIG. 10 being constrained within a transseptal dilator.
Figure 17A:
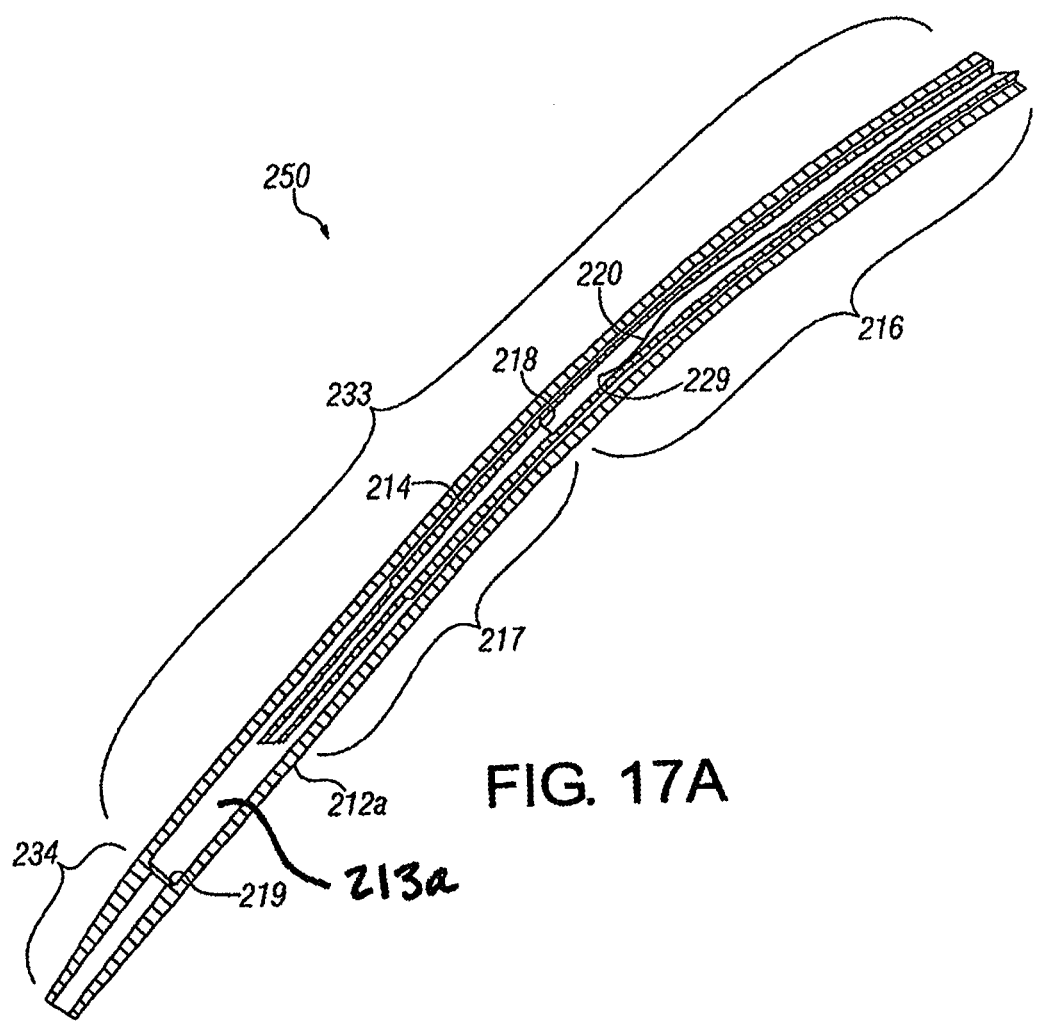
FIG. 17A is a cross-sectional side view of the transseptal guidewire shown in FIG. 10 being constrained within a transseptal needle of a transseptal access system.

Referring now to FIGS. 14, 15, 16, and 17A-17D, transseptal access to systems and methods of perforating an intra-atrial septum 104 (FIG. 1) are illustrated. As shown in FIG. 17A, a transseptal access system such as transseptal access system 250 may include an assembly of a dilator 212a and a transseptal needle 214. Alternatively, the transseptal access system may include either the dilator 212, 212a or the needle 214 alone or in combination with other components.

According to the embodiment illustrated in FIG. 15, the transseptal access system includes transseptal needle 214, which includes a wall 235 defining a lumen 215. The lumen 215 has a first section 216 and a second section 217 distal of the first section 216. A transition step 218 is defined between the first section 216 and the second section 217.

According to one exemplary method of perforating the intra-atrial septum, the transseptal guidewire 220 is inserted within the lumen 215 of the transseptal needle 214. Because the lumen 215 of the needle 214 has a diameter generally larger than the largest diameter of the transseptal guidewire 220, the elongate body 222 of the guidewire 220 may be urged into contact with the wall 235 of the needle 214 when the transseptal guidewire 220 is constrained in the lumen 215. This is a result of various factors, including the spring effect caused by the proximal curve formed in the transseptal guidewire, the general curvature of the needle 214 as it navigates the vasculature of a patient, and the rotation of the needle 214 and the transseptal guidewire 220 with respect to one another.

In order to reduce the possibility that the distal tip 229 of the transseptal guidewire 220 will engage or contact an interior surface of the transseptal needle 214, thus becoming caught or prevented from being advanced out of the lumen 215 of the needle 214 smoothly, the perforating tip 229 of the transseptal guidewire 220 is laterally offset from the longitudinal axis is (FIG. 12). Thus, when the transseptal guidewire 220 is inserted within the lumen 215 of the transseptal needle 214, the perforating tip 229 of the transseptal guidewire 220 is configured to be offset from the inner surface of the wall 235 of the transseptal needle 214. This offset distance is measured as the distance between the perforating tip 229 of the transseptal guidewire 220 and the surface of the wall, along a direction perpendicular to the surface of the wall. This distance is illustrated by the dimension "O" shown in FIG. 16

The distance between the wall 235 and the perforating tip 229 is equal to or larger than the transition step 218 defined between first section 216 and second section 217. This offset therefore reduces the tendency of the tip 229 to contact or engage the near-side transition step 218 (i.e., the transition step 218 closest to the wall surface from which the offset is measured). Additionally, the offset between the wall 235 and the perforating tip 229 is equal to or smaller than the sum of the transition step 218 and the inner diameter of the second section 217 to allow the perforating tip 229 to be advanced into the second section 217. This offset therefore reduces the tendency of the tip 229 to contact or engage the far-side transition step 218 (i.e., the transition step 218 farthest from the wall surface from which the offset is measured). Thus, contact between the perforating tip 229 and the wall 235 and transition step 218 of the transseptal needle 214 is reduced or avoided as the perforating tip is advanced through the lumen 215 from the first section 216 to the second section 217.

According to an exemplary embodiment of the transseptal needle 214, the first section 216 has a first inner diameter and the second section 217 has a second inner diameter that is smaller than the first diameter. For example, the diameter of the first section 216 of the transseptal needle 214 in an adult size may be about 0.032 inch and the diameter of the second section 217 may be about 0.020 inch. For such an adult needle 214, therefore, at the transition step 218 the diameter of the needle lumen 215 may change from about 0.032 inch to about 0.020 inch. The transition step 218 for such an adult needle 214 is about 0.006 inch and corresponds in size to half the difference between the diameter of the first section 216 and the diameter of the second section 217.

Similarly, the diameter of the first section 216 of the transseptal needle 214 in pediatric size may be about 0.027 inch and the diameter of the second section 217 may be about 0.013 inch, for example. For such a pediatric needle 214, therefore, at the transition step 218 the diameter of the needle lumen 215 changes from about 0.027 inch to about 0.013 inch. The transition step 218 is therefore about 0.007 inch for such a needle, corresponding in size to half the difference between the diameter of the first section 216 and the diameter of the second section 217.

According to one preferred embodiment, the perforating tip 229 of the transseptal guidewire 220 is configured to be offset from the inner surface of the wall 235 of the transseptal needle 214 a distance that is equal to or smaller than the second, smaller diameter of the lumen 215 of the transseptal needle 214, thereby reducing or avoiding contact between the perforating tip 229 of the transseptal guidewire 220 and the wall 235 as the perforating tip 229 is advanced distally through the transseptal needle 214. Also, the perforating tip 229 of the transseptal guidewire 220 is configured to be offset from the wall 235 of the transseptal needle 214 a distance that is equal to or larger than half the difference between the first diameter and the second diameter of the lumen 215 of the transseptal needle 214.

According to another embodiment, the perforating tip 229 of the transseptal guidewire 220 is configured to be offset from the wall 235 of the transseptal needle 214 a distance that is equal to or larger than the transition step 218 defined between the first and second sections 216, 217 of the lumen 215 of the transseptal needle 214, but equal to or smaller than the sum of the transition step 218 and the second diameter, thereby reducing contact between the perforating tip 229 and the transition step 218 as the perforating tip 229 is advanced through the lumen 215 from the first section to the second section of the lumen.

According to one exemplary embodiment best suited for use with an adult size transseptal access system, the perforating tip 229 of the transseptal guidewire 220 is configured to be offset from the wall of the transseptal access system a distance that is between about 0.01 inch and about 0.05 inch, a dimension selected depending on the size and type of access system. When the perforating tip 229 is in a relaxed configuration, the perforating tip 229 may be offset from the longitudinal axis 1a of the distal section 228 a distance [C] from about 0.01 to about 0.05 inch, again a dimension selected depending on the size and type of access system. In one preferred embodiment, the perforating tip 229 in the relaxed configuration is offset from the longitudinal axis 1a is a distance of about 0.03 in.

According to an exemplary embodiment best suited for use with a pediatric size transseptal access system, the perforating tip 229 of the transseptal guidewire 220 is configured to be offset from the wall of the transseptal access system a distance that is between about 0.005 inch and about 0.03 inch, a dimension selected depending on the size and type of access system. When the perforating tip 229 is in a relaxed configuration, the perforating tip 229 may be offset from the longitudinal axis 1a of the distal section 228 a distance [C] from about 0.005 to about 0.03 inch, again a dimension selected depending on the size and type of access system. In one preferred embodiment, the perforating tip 229 in the relaxed configuration is offset from the longitudinal axis 1a a distance of about 0.02 in.

Referring now to FIG. 16, an embodiment of the transseptal dilator 212, which is optionally used as a component of the transseptal access system 250, is illustrated. The transseptal dilator 212 has a wall 232 defining a lumen 213 that extends from a proximal section 230 to a distal opening 231. The lumen 213 of the dilator 212 is reduced in size from a first diameter in the proximal section 230 to a second diameter at the distal opening 231. The second diameter is generally smaller than the first diameter. For example, the diameter of the lumen 213 in the proximal section 230 may range from about 0.050 inch to about 0.065 inch. The distal opening 231, however, may have a smaller diameter than the proximal section 230 that may range from about 0.032 inch to about 0.038 inch.

According to an exemplary embodiment, the transseptal guidewire 220 is configured to be inserted into the lumen 213 of the transseptal dilator 212. When the transseptal guidewire 220 is constrained within the lumen 213, the perforating tip 229 is offset from the wall 232 of the dilator 212 by a distance [O] that is smaller than the diameter of the distal opening 231. For example, the offset distance [O] may be equal to or larger than half the difference between the diameter of the proximal section 230 and the diameter of the distal opening 231. According to an exemplary embodiment, for an adult system, the offset distance [O] is between about 0.01 inch and about 0.05 inch. For a pediatric system, however, the offset distance [O] may be between about 0.005 inch and about 0.03 inch. These offsets may vary depending on the size and type of the transseptal dilator 212 and other factors. This offset facilitates reducing or avoiding contact between the perforating tip 229 of the transseptal guidewire 220 and the wall 232 of the transseptal dilator 212 as the perforating tip 229 is advanced from the proximal section 230 and distally through the distal opening 231 of the transseptal dilator 212.

According to the illustrated embodiment in FIGS. 17A-17D, a transseptal access system 250 includes a transseptal needle 214 and a dilator 212a. The dilator 212a includes a first section 233 and a second section 234 distal of the first section 233. The lumen in the first section 233 has a diameter generally larger than the lumen in the second section 234, and a transition step 219 is defined between the first and second sections.

As shown in FIG. 17A, the transseptal needle 214 is inserted or positioned with the lumen 213a of the dilator 212a, and a transseptal guidewire 220 is constrained in the lumen 215 of the needle 214. As the guidewire 220 is advanced through the lumen of the needle 214, the perforating tip 229 of the guidewire 220 is offset from the wall of the needle 214 to prevent the guidewire 220 from being caught by the transition step 218. Additionally, the perforating tip 229 offset reduces or avoids contact of the perforating tip 229 against the wall of the second section 217 of the needle 214.

Figure 17B:
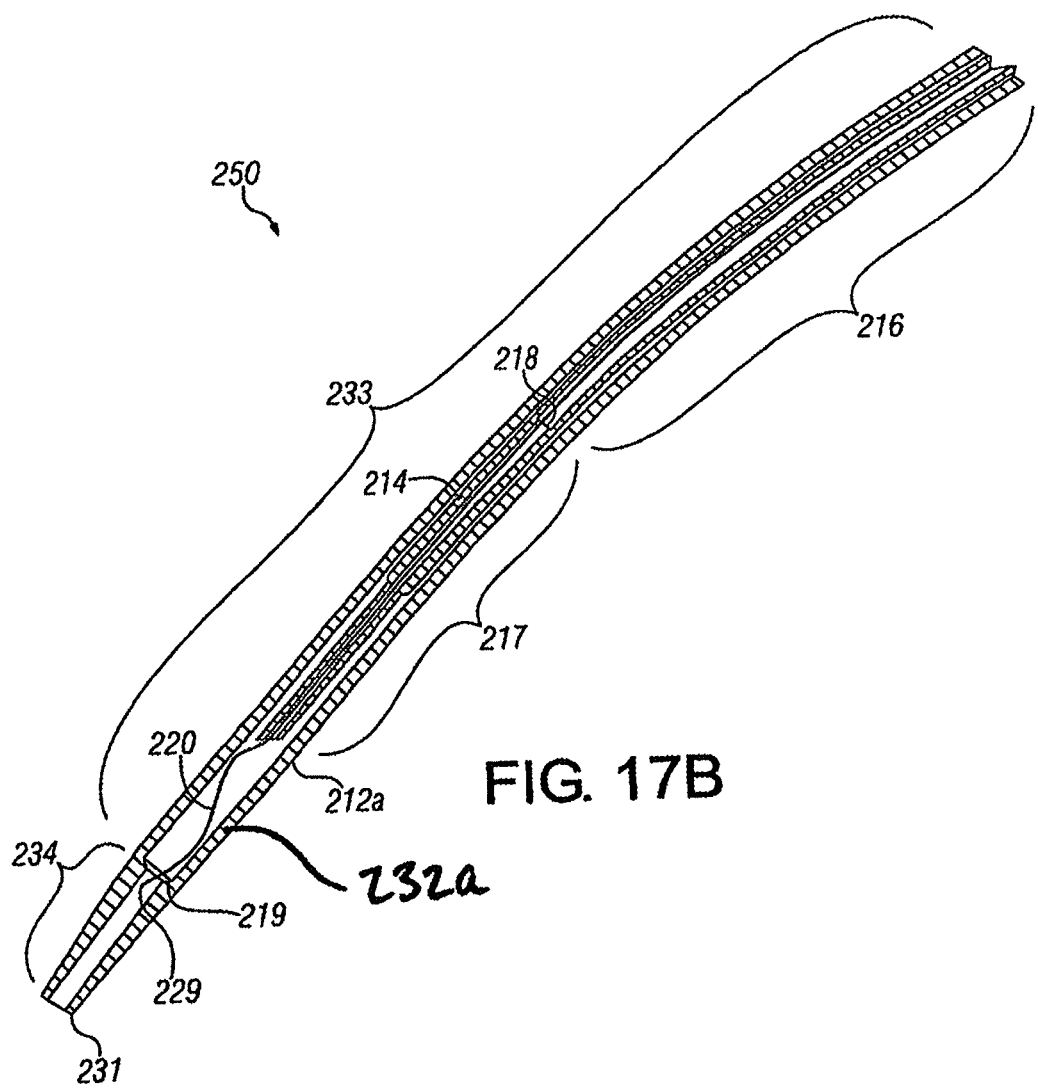
FIG. 17B is a cross-sectional side view of the transseptal guidewire shown in FIG. 10 being partially constrained within a transseptal dilator of a transseptal access system.

As shown in FIG. 17B, when the perforating tip 229 is advanced through the lumen (215, FIG. 15) of the needle 214 and into the lumen (213a, FIG. 17a) of the dilator 212a, a portion of the elongate body (222, FIG. 10) of the transseptal guidewire 220 contacts the wall of the dilator 212a. The perforating tip 229 is offset at a distance away from the wall of the dilator 212a so that it does not get caught in the transition step 219 of the dilator 212a. Additionally, the offset prevents or avoids contact of the perforating tip 229 against the wall of the second section 234 of the dilator 212a.

Figure 17C:
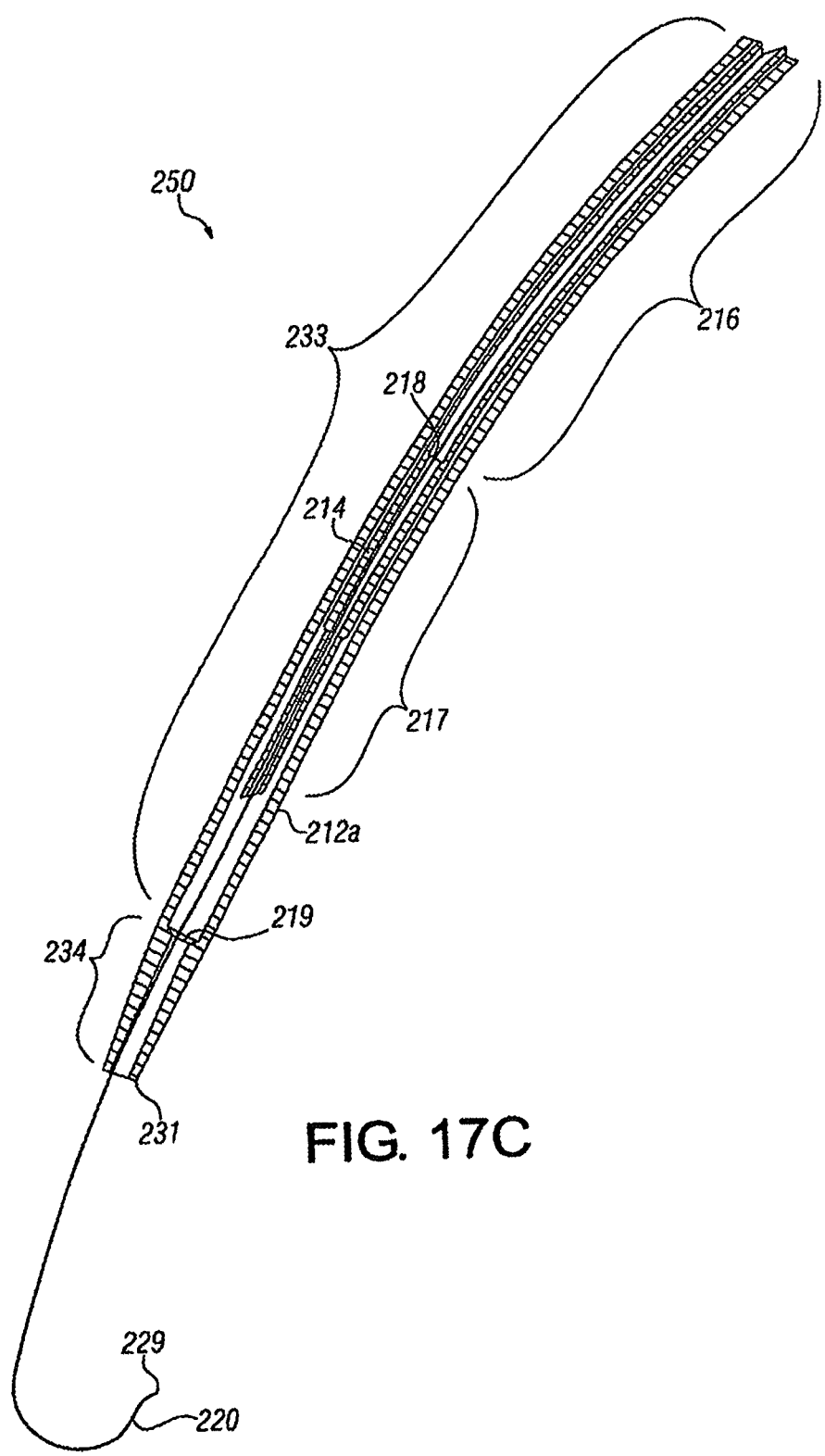
FIG. 17C is a cross-sectional side view of a distal portion of the transseptal guidewire shown in FIG. 10 extending from the transseptal access system in a relaxed configuration.

As shown in FIG. 17C, when the perforating tip 229 is advanced beyond the distal opening 231 of the dilator 212a, the transseptal guidewire 220 flexes or reverts to its relaxed configuration. As described above, in the relaxed configuration, the transseptal guidewire 220 is biased in a curved configuration to define a proximal curve (226a, FIG. 10) and a distal curve (228a, FIG. 10), such that the perforating tip 229 is offset from the longitudinal axis (1a, FIG. 12). Depending on the size of the lumen and the size of the transseptal guidewire 220, the offset of the perforating tip 229 in the relaxed configuration may be the same as or different from the offset of the perforating tip 229 from the wall of a lumen in which it is positioned in the constrained configuration. For example, the offset of the perforating tip 229 in the relaxed configuration (shown as distance [C] in FIG. 12) may be equal to or greater than or smaller than the offset of the perforating tip 229 from the wall of the dilator 212a (shown as distance "O" in FIG. 16) or the offset of the perforating tip 229 from the wall of the transseptal needle 214 (the distance from the wall 235 to the tip 229 measured in a direction perpendicular to the wall 235 in FIG. 15) in the constrained configuration.

When the distal curve 228a is unsupported (i.e., relaxed), the distal curve 228a renders the transseptal guidewire 220 less traumatic and reduces the depth of penetration of the tip 229 of the transseptal guidewire 220. This exemplary feature of transseptal guidewire 220 confers a significant benefit in that the distal second curve will not penetrate into the lateral left atrial wall because of the deflection is of the unsupported curve. It is beneficial to avoid or reduce such penetration in the event that the perforating tip 229 contacts the lateral left atrial wall, and the distal curve 228a reduces or eliminates the tendency for such penetration and/or limits the depth of any such penetration.

Figure 17D:
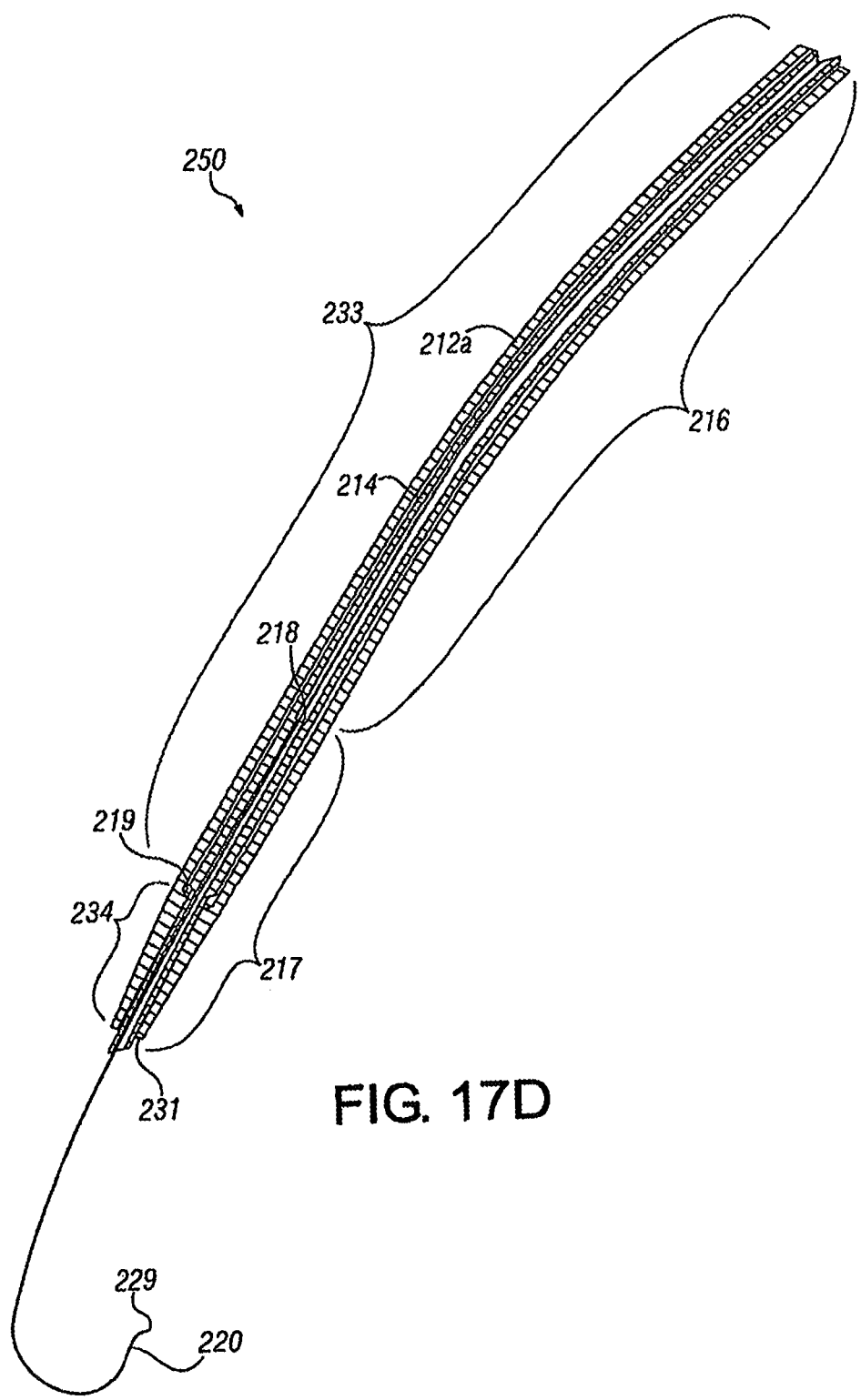
FIG. 17D is another cross-sectional side view of a distal portion of the transseptal guidewire shown in FIG. 10 extending from the transseptal access system in a relaxed configuration.

Referring now to FIG. 17D, after the transseptal guidewire 220 has perforated the fossa ovalis of the intra-atrial septum, the needle 214 may be advanced within the dilator 212a of the transseptal access system 250 so that a shoulder on an exterior surface of the needle 214 abuts the transition step 219 of the dilator 212a. Thus, a portion of the needle 214 may extend beyond the distal opening 231 of the transseptal dilator 212a and into a portion of the left atrium.

Accordingly, a surgical device is provided, according to exemplary embodiments of the invention, that reduces the risk of inadvertent perforation or trauma in transseptal procedures with the added benefit of confirming the puncture location prior to dilation. In particular, such embodiments provide accurate placement and safe access to the left atrium through the atrial septum. The device, according to exemplary embodiments, preferably performs with commercially available transseptal needle systems and allows for safer and easier penetration of a transseptal needle through the atrial septum. Furthermore, according to other exemplary embodiments of the invention, the surgical device reduces or prevents the device from catching on a surface on the inside of components of transseptal access systems. Thus, the device facilitates ease of use by physicians during such surgical procedures.

Although the invention is illustrated and described herein with reference to specific embodiments, the invention is not intended to be limited to the details shown. Rather, various modifications may be made in the details within the scope and range of equivalents of the claims and without departing from the invention.

What is claimed:

1. A method of forming a transseptal guidewire configured to perforate the intra-atrial septum, the method comprising the steps of:
   (a) forming an elongated body including a proximal section having a circular cross-section and an end section having a flattened outer cross-section;
   (b) forming a proximal curve in the end section of the elongated body having the flattened outer cross-section such that it is biased in a curved configuration, step (b) occurring after step (a);
   (c) forming a distal curve in a distal section of the end section such that it is biased in a curved configuration and oriented in a direction generally opposite that of the proximal curve thereby forming an S-shape, step (c) occurring after step (a);
   (d) forming a sharp pointed distal tip at an end of the distal section of the elongated body, the sharp pointed distal tip configured to perforate the intra-atrial septum; and
   (e) positioning at least one radiopaque marker on the elongated body in a location that is spaced from the distal tip, the distal curve and the proximal curve.

2. The method of claim 1, wherein the proximal curve and the distal curve occupy the same plane.

3. The method of claim 1, wherein the proximal curve and the distal curve occupy respective planes angled with respect to each other.

4. The method of claim 1, wherein the distal curve is formed by a bend or an angle in the distal section.

5. The method of claim 1, wherein the distal curve is formed by an arcuate portion of the distal section.

6. The method of claim 1, wherein an arclength of the proximal curve is larger than an arclength of the distal curve.

7. The method of claim 1, a maximum diameter of the elongated body being about 0.032 inch if used in conjunction with a dilator.

8. The method of claim 1, a maximum diameter of the elongated body being about 0.015 inch if used in conjunction with an outer needle.

9. The method of claim 1, the distal section of the transseptal guidewire having a longitudinal axis, the tip being laterally offset from the longitudinal axis, wherein the tip in a relaxed configuration is offset from the longitudinal axis a distance from about 0.01 to about 0.05 inch for an adult system.

10. The method of claim 9, the perforating tip in the relaxed configuration being offset from the longitudinal axis a distance of about 0.02 inch.

11. The method of claim 9, wherein the perforating tip in a relaxed configuration is offset from the longitudinal axis a distance from about 0.005 to about 0.03 inch for a pediatric system.

12. The method of claim 11, the perforating tip in the relaxed configuration being offset from the longitudinal axis a distance of about 0.01 inch.

13. The method of claim 1, the flattened outer cross-section of the end section being about 0.75 inch long.

14. The method of claim 1, the at least one radiopaque marker comprising a radiopaque coil.

15. The method of claim 1, wherein the distal curve renders the transseptal guidewire less traumatic when the distal curve is unsupported.

16. The method of claim 1, wherein the distal curve reduces the depth of penetration of the tip of the transseptal guidewire when the distal curve is unsupported.

17. The method of claim 16, wherein the depth of penetration is less than the length of the distal curve.

18. The method of claim 1, wherein at least a portion of the end section formed in step (a) has a first outer dimension in a first direction transverse to a longitudinal axis of the elongated body that is larger than a second outer dimension in a second direction transverse to the longitudinal axis.

19. The method of claim 18, the first dimension being between about 0.008 and about 0.014 in.

20. The method of claim 19, the first dimension being about 0.011 in.

21. The method of claim 18, the second dimension being less than about 0.008 in.

22. The method of claim 21, the second dimension being about 0.005 in.

23. The method of claim 1, a maximum diameter of the elongated body being about 0.050 or about 0.015 in if used in conjunction with an outer needle.

24. The method of claim 1, at least a portion of the end section being ovalized.

25. The method of claim 24, the ovalized portion of the end section being about 0.75 inches long.

26. The method of claim 1, the at least one radiopaque marker comprising a band, or coil.

27. The method of claim 26, the band or coil being mounted by adhesive.

28. The method of claim 27, wherein the adhesive comprises a low viscosity cyanoacrylate.

29. The method of claim 26, the band or coil being mounted by swaging.

30. The method of claim 26, the band or coil having a circumference not exceeding the maximum circumference or perimeter of the end section.

31. The method of claim 30, the band or coil having an outer diameter greater than about 0.010 in.

32. The method of claim 26, the band or coil having an inner diameter smaller than the first dimension of the end section.

33. The method of claim 30, the band or coil having an inner diameter less than about 0.011 in.

34. The method of claim 1, the radiopaque marker comprising a platinum/iridium alloy.

35. The method of claim 1, wherein the elongate body comprises superelastic nitinol material.

* * * * *